(12) United States Patent
Janét et al.

(10) Patent No.: US 9,664,813 B2
(45) Date of Patent: May 30, 2017

(54) AUTOMATED INSECT MONITORING SYSTEM

(71) Applicant: Delta Five, LLC, Raleigh, NC (US)

(72) Inventors: Jason André Janét, Raleigh, NC (US); William Stockton Howell, Raleigh, NC (US); Stephen Paul Land, Cary, NC (US); Robert W Winston, III, Raleigh, NC (US); Lisa Ann Lyons, Hillsborough, NC (US)

(73) Assignee: Delta Five, LLC, Raleigh, NC (US)

( * ) Notice: Subject to any disclaimer, the term of this patent is extended or adjusted under 35 U.S.C. 154(b) by 292 days.

(21) Appl. No.: 14/621,673

(22) Filed: Feb. 13, 2015

(65) Prior Publication Data

US 2016/0238737 A1    Aug. 18, 2016

(51) Int. Cl.
*G01N 21/00*    (2006.01)
*G01V 8/12*    (2006.01)
(Continued)

(52) U.S. Cl.
CPC .............. *G01V 8/12* (2013.01); *A01M 1/023* (2013.01); *A01M 1/026* (2013.01); *A01M 1/04* (2013.01);
(Continued)

(58) Field of Classification Search
CPC ...... A01M 99/00; A01M 1/023; A01M 1/026; A01M 1/04; A01M 1/103; A01M 1/14; G01N 35/00; G01V 8/12
(Continued)

(56) References Cited

U.S. PATENT DOCUMENTS

| | | | |
|---|---|---|---|
| 5,878,526 A | 3/1999 | Brigalia et al. | |
| 6,724,312 B1 | 4/2004 | Barber et al. | |
| 6,914,529 B2 | 7/2005 | Barber et al. | |
| 7,020,996 B2 | 4/2006 | Beroza et al. | |
| 7,212,112 B2 | 5/2007 | Barber et al. | |
| 7,212,129 B2 | 5/2007 | Barber et al. | |
| 7,262,702 B2 | 8/2007 | Barber et al. | |
| 7,348,890 B2 | 3/2008 | Barber et al. | |
| 7,395,161 B2 | 7/2008 | David et al. | |
| 7,591,099 B2 | 9/2009 | Lang et al. | |
| 7,719,429 B2 | 5/2010 | Barber et al. | |
| 8,211,419 B2 | 7/2012 | Siljander et al. | |
| 8,375,626 B2 | 2/2013 | Borth et al. | |
| 8,661,728 B2 | 3/2014 | Borth et al. | |
| 8,830,071 B2 | 9/2014 | Borth et al. | |
| 2009/0145019 A1 | 6/2009 | Nolen et al. | |
| 2010/0212213 A1 | 8/2010 | Hope, III et al. | |
| 2011/0041385 A1 | 2/2011 | Faham et al. | |
| 2013/0042520 A1 | 2/2013 | Snell et al. | |
| 2013/0180162 A1 | 7/2013 | Vasudeva et al. | |
| 2013/0208114 A1 | 8/2013 | Balsam | |

(Continued)

FOREIGN PATENT DOCUMENTS

WO    2013137919 A1    9/2013

OTHER PUBLICATIONS

Unknown, Author, "Warning—Bed Bugs are coming!", Global PBS, Polymodal Biological Sensors, Accessed Apr. 20, 2015, Available online at: http://globalpbs.com/English/globalpbs_technology.doc, 1-4.

*Primary Examiner* — Tri T Ton
(74) *Attorney, Agent, or Firm* — Murphy, Bilak & Homiller, PLLC

(57) ABSTRACT

A discrete and safe automated insect monitoring system includes a housing, an interior chamber within the housing, and a light source arranged within the housing to illuminate at least a portion of a floor surface of the interior chamber. A multi-pixel optical sensor is arranged within the housing so that a field of view of the sensor comprehends a substantial portion of the floor surface. A processing circuit arranged within the housing receives optical data from the multi-pixel optical sensor, analyzes the optical data to detect the intrusion of an insect or other object into the interior chamber by comparing most recently received optical data to previously received optical data, and generates an indication in response to detecting the intrusion of an insect or other object. Detection and/or classification results can be wirelessly forwarded to another device, to alert appropriate personnel.

19 Claims, 17 Drawing Sheets

(51) Int. Cl.
    *A01M 1/02*     (2006.01)
    *A01M 1/04*     (2006.01)
    *A01M 1/10*     (2006.01)
    *A01M 1/14*     (2006.01)
    *A01M 99/00*     (2006.01)
    *G01N 35/00*     (2006.01)

(52) U.S. Cl.
    CPC .............. *A01M 1/103* (2013.01); *A01M 1/14* (2013.01); *A01M 99/00* (2013.01); *G01N 35/00* (2013.01)

(58) Field of Classification Search
    USPC ......... 356/237.1–237.6, 238.3, 239.1–239.8, 356/241.1–241.6
    See application file for complete search history.

(56) References Cited

U.S. PATENT DOCUMENTS

2013/0223677 A1    8/2013    Ots et al.
2016/0235050 A1*  8/2016    Janet ..................... A01M 1/023

* cited by examiner

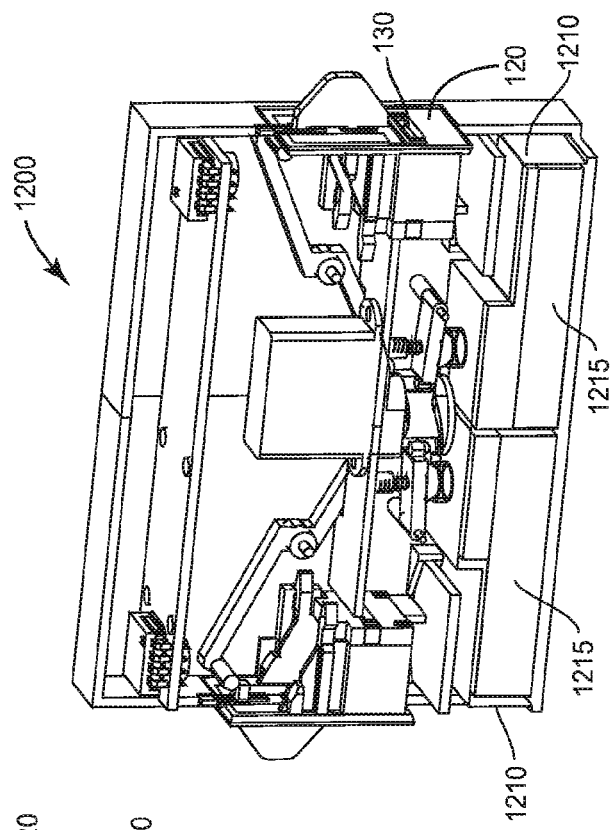
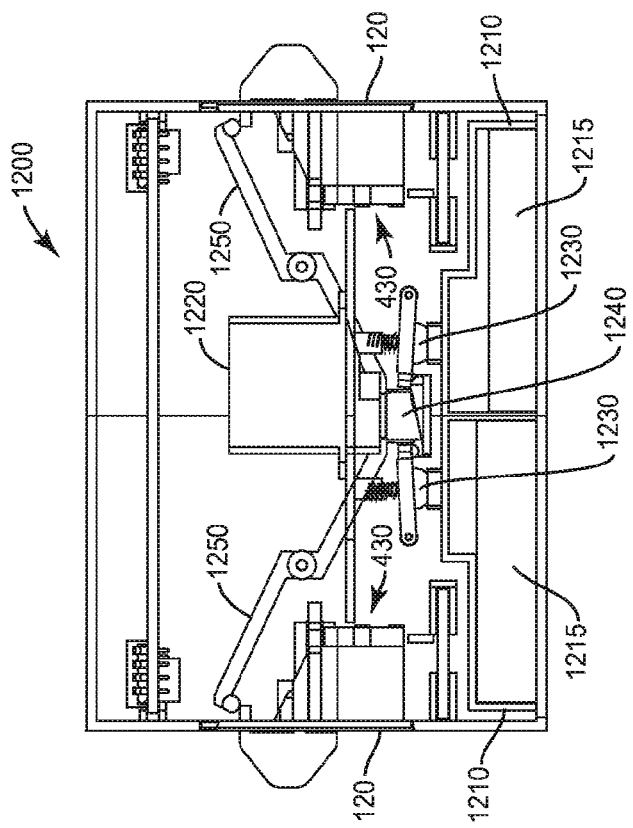
FIG. 12A
FIG. 12B

AUTOMATED INSECT MONITORING SYSTEM

TECHNICAL FIELD

The present disclosure generally relates to pest control, and more particularly relates to the detection of bedbug infestations.

BACKGROUND

Indoor insects are considered "pests" because they can be nuisances and a source or symptom of health risks. Detecting pests is the first step to know a problem exists. Classifying them is essential to prescribe and implement an appropriate treatment. Doing both quickly can prevent infestations.

Personally encountering pests is one way to both detect and classify. People may readily see or feel ants, flies, gnats and mosquitoes because these insects make little effort to conceal their presence. People may also see cockroaches, fleas and bedbugs, but more effort or chance is required because they are nocturnal, very small and/or hide out-of-sight. Seeing and feeling insects, in general, can invoke visceral reactions, rational or not. Being bitten or stung can also result in physical reactions. Thus, people generally prefer to not encounter pests at all, especially in their living spaces.

Traps rarely eradicate pests, but can reduce encounters between pests and humans. Conventional traps tend to require significant human effort to inspect, detect and classify incarcerated insects or remains thereof. Traps also do not provide any indication when pests enter them; significant time may elapse between inspections, allowing infestations to propagate.

Conventional traps can also be obtrusive and dangerous. For example, they may occupy significant space in plain sight, produce odors, release toxins, and ensnare children or pets.

Conventional traps can also be expensive. Many traps on the market cost several tens of dollars and still require human labor to frequently inspect them. Some traps even require chemicals and dyes to lure and/or illuminate trace indications of pests; this compounds the associated labor requirements.

For several reasons, bedbugs are of particular concern to homeowners as well as hospitality and transportation industries. Considered more of a nuisance than a health hazard, bedbugs lurk in dark crevices of living spaces. Bedbugs are small, flat, wingless insects with six legs that, like mosquitoes, fleas, mites and biting gnats, feed exclusively on blood from animals and humans. They range in color from nearly white to brown, and they turn rust-red after feeding. The common bedbug is usually less than 0.2 inches (5 mm) in length, making it easy to miss with the naked eye. Bedbugs are so named because they mostly hide in bedding and mattresses.

Bedbugs are commonly found in hotels, hostels, shelters, apartment complexes, cruise ships, buses, airplanes, trains, and waiting rooms, all of which are places where multiple people may pass through and/or stay for brief periods of time. Bedbugs are nocturnal and can hide in beds, floors, furniture, wood and paper trash during the day. Because bedbugs hide in small crevices, they can stow away in or on luggage, pets, furniture, clothing, boxes and other objects. Bedbugs may relocate from their original luggage homes to adjacent luggage in cargo holds, causing further spread.

Bedbugs are found worldwide, but are most common in developing countries. And, not surprisingly, bedbugs are most noticed in areas of greater human concentration.

In the U.S., it is estimated that there are approximately 500-million dwelling spaces that could potentially harbor bedbugs. These include approximately 10 million hotel/motel beds, 40 million dorm rooms and apartments, and 350 million other residential rooms. Other spaces where infestations might occur include rental rooms in vacation properties, ships, ferries, buses, and passenger train cars.

Bedbugs have an average life span of 6 to 12 months, but can survive in certain environments for up to four years. They only feed on blood, through all life stages, and require one or more blood feedings to progress to each of several life stages. Bedbugs can go weeks without feeding.

The table below indicates the lengths and habits of bedbugs at various life stages.

TABLE 1

| Stage | Length | Comments |
| --- | --- | --- |
| Egg | 1 mm | Eggs hatch within 6-10 days, and hatchlings immediately seek blood meal |
| $1^{st}$ Instar | 1.5 mm | Takes a blood meal, then molts |
| $2^{nd}$ Instar | 2 mm | Takes a blood meal, then molts |
| $3^{rd}$ Instar | 2.5 mm | Takes a blood meal, then molts |
| $4^{th}$ Instar | 3 mm | Takes a blood meal, then molts |
| $5^{th}$ Instar | 4.5 mm | Takes a blood meal, then molts |
| Adult | 5.5 mm | Takes repeated blood meals over several weeks |
| Adult Male | 5.5-6.5 mm | Increases length by ~20% when engorged, mates continuously |
| Adult Female | 5.5-6.5 mm | Females lay up to 5 eggs per day continuously |

Peak bedbug biting activity is usually just before dawn. They can feed without waking their unwitting hosts. Meals are procured in as little as three minutes, after which the bedbugs are engorged and detach from their host, crawling into a nearby hiding place to digest their meal. Hosts typically do not feel their bites because bedbugs inject a numbing agent into the body, along with an anticoagulant to keep blood flowing as they extract it. The first sign of bedbug bites may be itchy, red bumps on the skin, usually on the more readily-accessible upper torso arms or shoulders. Bedbugs tend to leave straight rows of bites. Bedbug bites do not usually require treatment, although secondary infections can occur. Some people do have allergic reactions to bedbug bites, requiring medical attention.

Hosts passively lure bedbugs and other blood-consuming pests in multiple ways, but research has shown that the most effective attractants are heat and carbon dioxide ($CO_2$). Most conventional traps are passive, and rely on bedbugs falling into inescapable spaces or sticking to adhesive surfaces that interrupt their traffic patterns between perceived hosts and hiding places. Some traps are more active, however, and attempt to emulate host-like heat and $CO_2$ generation; they may also include pheromones, kairomones and various other chemicals. Unfortunately, traps like these can have drawbacks. First, generating or releasing $CO_2$ elevates the toxicity inside a living space. Second, because humans can generate upwards of 40 liters of $CO_2$ each hour, bait chambers can be very bulky and rely on unstable or offensive chemical reactions to emulate human-level signatures.

Third, refreshing the bait(s) can be expensive due the cost of the chemicals and labor. Fourth, such chemicals can be offensive and potentially toxic to humans and pets.

Quality hoteliers strive to provide guests with positive experiences. Steps are regularly taken to ensure that living spaces are hygienic, neat, affordable, and inoffensive. Hoteliers are very concerned about guest perceptions, in part because consumers rely heavily on reviews, which social media have made more voluminous and available. Hoteliers are also concerned about liability. And, of course, hoteliers are concerned about costs, whether from lost revenues or pest search-and-eradicate steps. Notably, some eradication steps require the destruction and removal of expensive furniture, fixtures and equipment. Note that false reports of bedbugs may cause expensive eradication steps to be taken unnecessarily.

Many consumers associate bedbugs and other pests with a lack of cleanliness. In truth, spaces may be "clean" per strict hygienic standards yet still host bedbugs, because bedbugs can be ushered into spaces by even the cleanest of hosts. While conventional "cleanliness" may not prevent bedbugs, an argument could be made that the presence of any pests constitutes a lack of cleanliness. This argument becomes more compelling when consumers realize that bedbugs discharge blood-based waste, lay up to five eggs per-day/per-female, deposit exoskeletons when they molt, and leave carcasses when they die.

Some consumers may also fear that bedbugs and other pests could facilitate communicable diseases, despite CDC claims to the contrary. After all, these pests extract, digest and eliminate trace elements of blood. In fact, a tell-tale sign that bedbugs reside in a space can be found in the bloodstains they leave, especially along the seams of mattresses. Bedbugs also leave dark spots of blood-based waste where they might crawl into hiding places on furniture, walls, and floors. Given the gravity of certain blood-borne diseases, even if the blood is digested and dried, it is easy to understand this fear.

Hoteliers understand and respect these concerns and the costly ramifications of a bad guest experience. Litigation is expensive. Medical bills are expensive. Lost loyalty is expensive. A tarnished reputation is expensive. And bedbug eradication is expensive. To the latter point, infestations can cost hoteliers hundreds and thousands of dollars per occurrence, with multiple occurrences possible annually.

To minimize the impact of litigation, hoteliers may wish to know not only whether pests of any kind are present but also which pests are present. Should any claims be made by guests, hoteliers will want to have verifiable information about which insects, if any, could have bothered the guests. One cannot necessarily assume bites are from bedbugs, or that the bites were even suffered while the guests were in the hotel. Bites can be hard to identify, even for doctors. It is best to collect and identify pests to identify the possible source of the bites.

Bedbug infestations can occur in a matter of weeks. While insecticides are available, they cannot be applied to areas that come in direct contact with skin, due to their toxicity. Also, modern bedbug populations are highly resistant to the insecticides used for their control. Freezing and very high temperatures can kill bedbugs without toxicity, but are infeasible as a preventative measure for living spaces. Similarly, Sterifab® kills bedbugs on contact, but does not leave residues and therefore cannot be used for preventative treatment.

SUMMARY

Embodiments of the present invention provide a discrete and safe automated insect monitoring system that can attract, capture, detect, and identify insects and communicate its findings quickly. Because of its low cost and unobtrusiveness, the insect monitoring system described herein is particularly useful for the hospitality industry, and broadly useful for transportation, residential, and other market segments.

A discrete and safe automated insect monitoring system according to some embodiments of the systems described herein includes a housing, an interior chamber within the housing, and a light source arranged within the housing to illuminate at least a portion of a floor surface of the interior chamber. A multi-pixel optical sensor is arranged within the housing so that a field of view of the sensor comprehends a substantial portion of the floor surface. A processing circuit arranged within the housing receives optical data from the multi-pixel optical sensor, analyzes the optical data to detect the intrusion of an insect or other object into the interior chamber by comparing most recently received optical data to previously received optical data, and generates an indication in response to detecting the intrusion of an insect or other object. Detection and/or classification results can be wirelessly forwarded to another device, in some embodiments, to alert appropriate personnel.

BRIEF DESCRIPTION OF THE FIGURES

FIGS. 12A and 12B are cut-away views of another example insect monitoring system.

DETAILED DESCRIPTION

Figure 1:
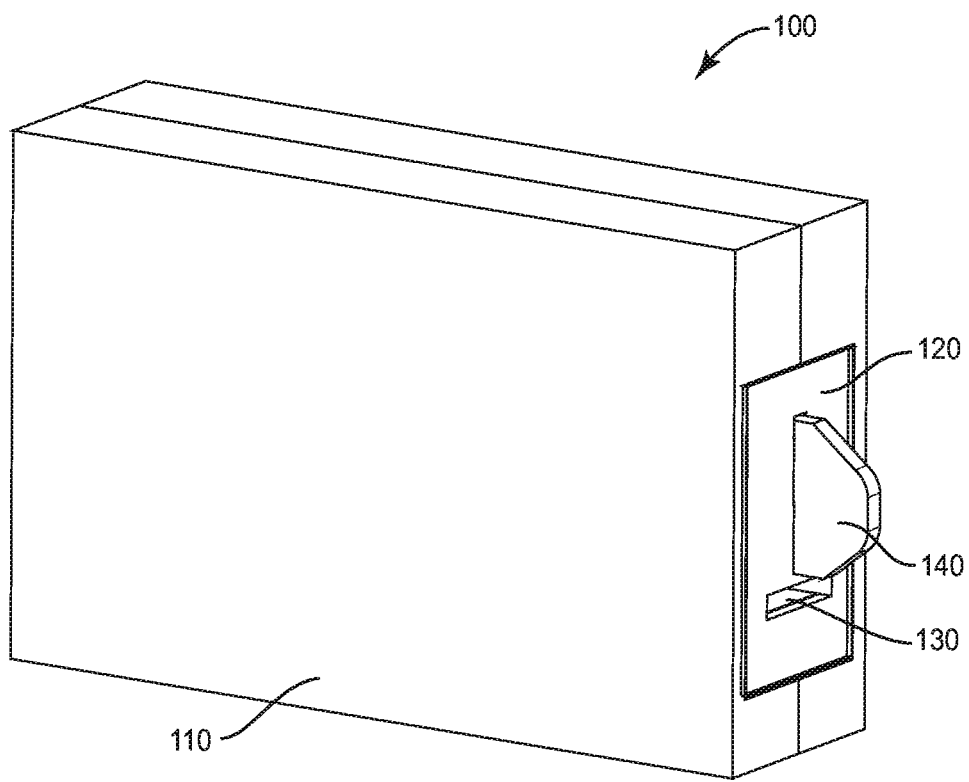
FIG. 1 illustrates an example insect monitoring system according to some embodiments of the present invention.

In view of the pest infestation issues described above and the particular issues faced by vendors in the hospitality industry, a pest trap should embody the following features:

Safety: Traps should pose no risk to the environment or its inhabitants.

Discretion: Traps should remain inoffensive to all of the senses (sight, sound, smell, touch and taste), and not arouse unwarranted suspicion.

Remote Notification: Traps should be able to discretely communicate detection and/or classification results in a timely manner to parties with a need-to-know, without drawing unwanted attention and without requiring unnecessary labor.

On-Board Detection: Traps should be able to autonomously detect intruders without requiring outside intervention from humans, be they on-site or remote.

On-Board Classification: Traps should facilitate autonomous classification of detected intruders without requiring outside intervention from humans, be they on-site or remote.

Cost-Effective: Traps should perform the aforementioned tasks and remain comparable in cost to existing, though generally less-capable, alternatives, to provide benefit to the end-user.

Minimize False-Positives: Traps that ultimately require human intervention should provide a means of minimizing the occurrence of false positives and/or give notified humans the ability to remotely reset any false positives. Note that canines are attributed with ~80-95% accuracy for bedbug detection, whereas human inspectors are attributed with 60-80% accuracy.

Leverage Organic Lures: To maximize safety and effectiveness, traps should strive to utilize only chemical attractants that naturally exist in spaces, and without elevating toxin levels.

Unfortunately, no existing indoor insect pest trap is capable of providing most, if not all, of these features.

The innovative traps described herein are designed to address a priority bedbug problem for hoteliers. However, as discussed above, hotel rooms in the U.S. are a mere fraction of the total spaces that could benefit from this invention. Moreover, the traps and techniques described herein are not limited in application to bedbug detection, but may be applied to other indoor insect pests as well.

Various embodiments of the autonomous insect monitoring system described herein include several or all of the features described below.

Safety—A crevice-like entry port to the interior of the trap is too small for human or pet access, but ideally sized for insects. The primary bait may be a combination of heat, infrared (IR) light, and a crevice-like entry port, all of which are benign. Secondary bait, in some embodiments of the inventive monitoring systems disclosed herein, is $CO_2$, which is naturally exhaled from host(s) and which can be captured at a point near or below their heads. ($CO_2$ is heavier than air and, thus, sinks after being exhaled.) In some embodiments, as described in further detail below, chemical baits may be passively or controllably dispersed. Insects that enter an interior chamber of a monitoring system as described herein, which interior chamber acts as a "photo booth," are entrapped on its floor by adhesives, fabric snares, gravity, slick walls, an out-of-reach port, a closable door, chemical and/or mechanical arrestants, or some combination thereof, in various embodiments. The electronics in the traps detailed herein are low-voltage and thus inherently safe—in contrast, some conventional traps on the market are actually embedded in AC voltage power strips, which can cause high-voltage shock.

Non-Pest Object Rejection—Other features of some embodiments of the monitoring systems detailed below are intended to minimize the likelihood that non-pest objects may enter the photo booth. These include, for example: (1) the use of a minimal aperture—the crevice-like entry port is sized for very small insects, minimizing the opportunity for dust, lint, and other foreign objects to enter; and (2) outflow—heat from the trap's electronics, particularly components at or near the photo booth floor, will rise inside the photo booth and be channeled through the crevice-like port (like a chimney); combined with a filtered air intake located away from the crevice-like port, and near or below the heat-generating components, this will create a continuous outflow of warm, clean air that will push suspended airborne objects away from the port and, thus, prevent them from entering the photo booth to produce false positive detection and/or classification results.

Discretion—The traps described herein can be approximately the size of a deck of playing cards. This is significantly smaller than conventional traps. The traps can thus be deployed in small spaces, preferably behind or under the headboard or bedside tables. These locations are advantageous because they are near hosts' upper bodies and where breath elements, particularly heat and $CO_2$, may be concentrated. The traps may use wireless communications (i.e., optical and/or radio-frequency communication links) to convey data; alarm-like audible or visual alerts are generally not used, but may be included in some embodiments. Some embodiments of the insect monitoring system use benign doses of attractants and arrestants where possible, so as to not release offensive odors or toxins. For instance, infrared (IR) light, which attracts bedbugs but is invisible to humans, may be used to illuminate the photo booth, in some embodiments. Trap colors and labels are preferably low-profile, so as to not arouse unwarranted suspicion or concern.

Remote Notification—Embodiments of the traps described herein discretely convey detection and classification results via wireless communications, e.g., over optical and/or radio-frequency communication links; the use of alarm-like audible signals or lights is generally avoided. The traps may be network topology-agnostic, because they may be programmed and fitted to interface with a plethora of industry-standard network configurations, protocols and reference models. Communication topologies and techniques may include, but are not limited to, direct-to-access-point, multi-hop, query-response, multi-cast, etc. The traps discretely communicate, in a timely manner, detection and/or classification results to parties with a need-to-know, without drawing unwanted attention, and without requiring unnecessary labor. If operators desire more than the high-level detection/classification messages, some embodiments of the traps may receive and fulfill requests for additional information including, for example, pre- and post-processed images of insects caught in the traps.

Autonomous On-Board Detection—Unlike conventional traps, the presently disclosed traps include optical sensors configured to capture multi-pixel images of insects intruding into the interior space of the trap. The traps include circuitry that performs on-board processing to detect changes in captured images and image features indicative of insects. The number of pixels may range from four to 1000, in various embodiments. This relatively small number of pixels keeps the required processing power for onboard processing to reasonable levels, allowing the use of inexpensive and power-efficient processing circuits. Visible, infrared, and/or other illumination of the interior chamber may be used, to enhance the captured optical images. Because the traps are designed to ensure that insects become trapped in the invention's "photo booth," image capture and process intervals may occur at slow frame rates, to minimize energy consumption by the device. Systems may be configured to enter SLEEP and/or POWER-OFF modes to further conserve energy.

Structured Lighting—The traps may use one or combinations of several structured lighting approaches. First, to enhance contrast, some embodiments use backlighting, e.g., through a floor of the interior chamber, opposite to the imaging sensor, to produce silhouette images. Some embodiments may use angled lighting, to create shadows and enhance dimensionality. Some of these and some other embodiments may use flood lighting, to illuminate insects in the "photo booth" and to allow their features to be distinguished. Combinations of these techniques may also be used. Infrared (IR) lighting may be used, in some embodiments—in addition to its ability to lure bedbugs, tuning the imaging system to IR light can make the imaging less vulnerable to changes in ambient light, which can enter the photo booth through the crevice-like port.

Onboard Image Pre-Processing—In various embodiments of the inventive insect monitoring system described herein, any combination of background subtraction, noise filtering, contrast enhancement, global or local thresholding, and morphological opening may be applied to the images captured within the system. Background subtraction computes the foreground of the image for analysis. Background subtraction could be implemented as simply as subtracting some original image, but, more likely, the background to be subtracted will be a weighted average of a series of previous images. Noise filtering may include one or more of several techniques, such as temporal filtering or spatial filtering via a low-pass filter. Noise reduction may occur before or after background subtraction. Light compensation and contrast enhancement may be applied, including, for example, intensity normalization, dynamic range compression, and/or histogram equalization algorithms. Then, a morphological opening may be applied to the resulting image in order better define the individual insects, if there is more than one. A global threshold calculated from the image histogram or local thresholds based on values of nearby pixels may be applied to the resulting image.

Onboard Region Identification—In some embodiments, basic detection of an insect is based on background subtraction only. Contrast detection or a high-pass filter may also be used, where gradients are calculated to define boundaries between objects and the background. In some embodiments, blob detection may also be employed to identify groups of adjacent pixels that may be indicative of one or more pests. Blobs are connected components that can be found using various techniques such as region growing. The results of this detection are frequently called regions of interest (ROIs) or just regions. As bedbugs have the tendency to become translucent when unfed, some regions may contain "holes." Some embodiments may use a hole-filling procedure or morphological closing to remove these holes.

Onboard Region Description—There are a number of ways to determine whether a region of interest contains an insect or some other benign object. Each region has a number of descriptors that define properties of the region as a whole. These descriptors include color or grayscale histograms for the region, the shape of the region, size of the region, aspect ratios of the region, centroid of the region and other regional moments. Some embodiments of the automated insect monitoring system calculate these descriptors for regions of interest and compare them to known descriptors for common pests. The area occupied by an intruder, defined as the number of pixels in a blob or inside a boundary (also known as "hull") may be used to define insects. Similarly, the perimeter of a region of interest, defined as the number of pixels along the boundary, may be used to identify insects. Aspect ratios, defined as ratios of the blobs' length-to-width, major-to-minor axis variance, or major-to-minor eigenvalues, can also be used to characterize a region of interest and then to identify insects.

Negative Feedback—Embodiments of the insect monitoring system may receive feedback from remote or proximal operators, including the results of background subtraction. Examples of feedback include, but are not limited to (1) indicators of dead pixels, likely malfunctioning photo-sites, which can be subsequently ignored so as to not be confused with pests; (2) indicators of non-pest objects, likely inert objects (e.g., lint, dust, airborne particles, etc.) that enter the photo booth, which can be subsequently ignored so as to not be confused with pests.

Autonomous On-Board Classification—Once a region of interest has been determined to contain an insect, it is useful to classify the type of insect, to correctly combat the infestation. In some embodiments, the onboard processing is adapted to perform autonomous classification of detected intruders in order to differentiate among several types of insects and/or among distinct stages of an insect's lifecycle. This implementation may include comparison of one or more region descriptors described above to stored profiles for two or more types or stages of insects. Once again, classification may be performed without requiring outside intervention from humans, whether on-site or remote. Methods of comparison may include simple differencing techniques and principle component analysis (PCA). Other moment-based techniques, including raw, central, scale-invariant, rotation-invariant and translation-invariant may also be used. Template matching may be used, in some embodiments, where one or more convolution kernels may be applied to regions of the image to detect similar patterns. Templates can be shapes of features or of entire insects, which may be "AND'ed" with the image at different rotations and at different scales. In some embodiments, a clustering or nearest-neighbor algorithm may be employed for classification. The error metrics for any of these algorithms might include a diverse set of region descriptors.

Advantages of some embodiments of the automated insect monitoring systems described herein include that the systems are cost-effective. The monitoring systems provide unattended pest detection, unlike alternative technologies, and can do so at a similar cost.

The insect monitoring systems also provide superior performance. The systems can be placed very close to hosts without offending or being a hazard and thus can leverage hosts' naturally-occurring attractants due to proximity. In some configurations and deployments, the monitoring systems can also leverage hosts' naturally-occurring attractants by drawing $CO_2$ into the photo booth, and exhausting it through the crevice-like port. Some embodiments can generate IR light, which is absorbed by $CO_2$ and thus acts as a lure for bedbugs. Some embodiments may generate heat, like mammalian hosts, which originates and is concentrated in the photo booth and exhausted through the crevice-like port. The crevice-like ports of the monitoring systems attract pests, like bedbugs, that seek nooks in which to hide. In some embodiments, additional baits can be placed inside the photo booth.

The monitoring systems can also be operated at low costs. Savings in operating costs per system are realized primarily through reduced labor, but may also include accrue from reduced bait costs and from the value of early detection and intervention (i.e., early detection may prevent infestations). When multiplied by dozens, perhaps thousands, of rooms in a property or group of properties, these cost savings can be significant.

Figure 2:
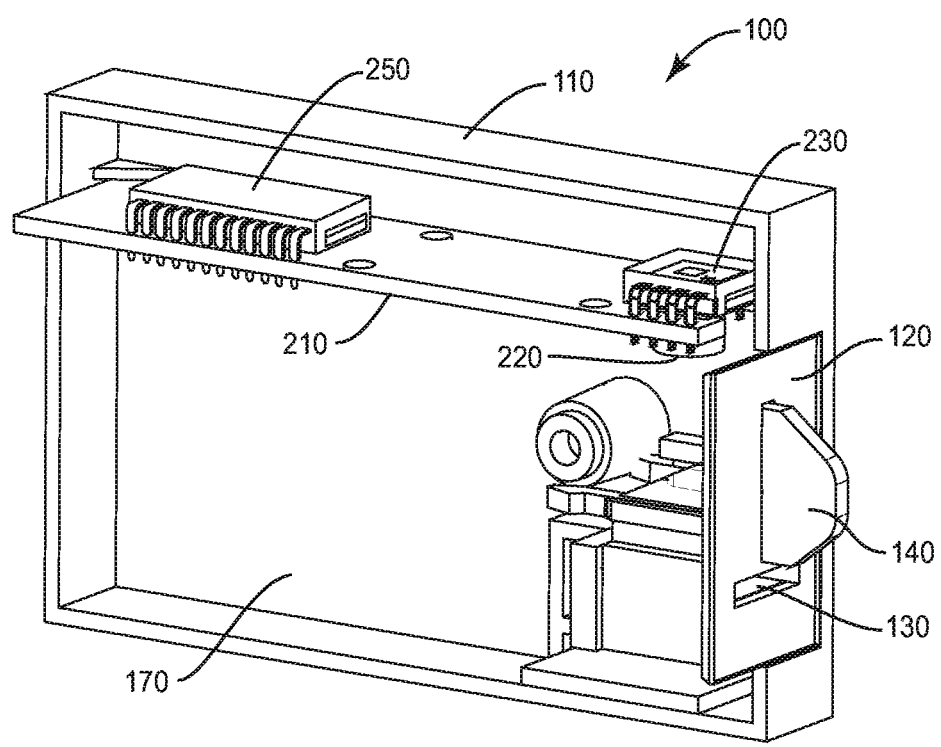
FIG. 2 is a cut-away view of the insect monitoring system of FIG. 1.
Figure 3:
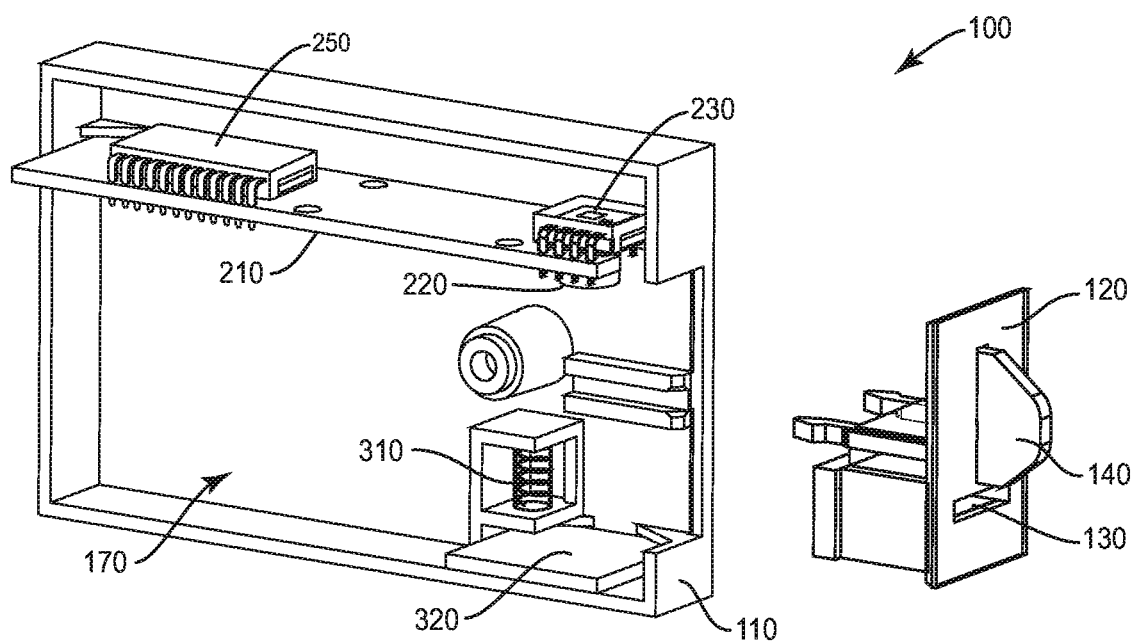
FIG. 3 illustrates the insect monitoring system of FIG. 2 after removal of a removable chamber portion.
Figure 4A:
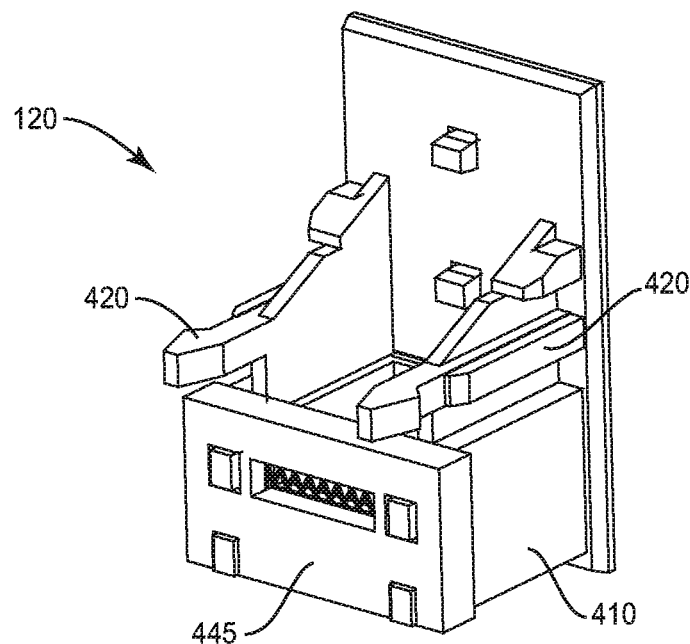
FIGS. 4A, 4B, 4C, and 4D illustrate details of an example removable chamber portion.
Figure 4B:
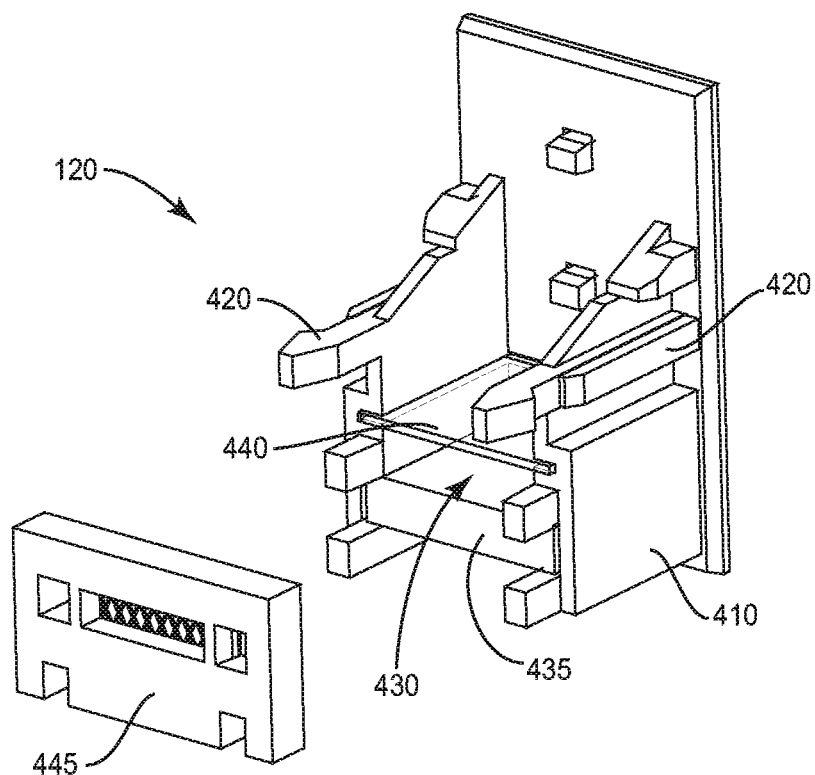
Figure 4C:
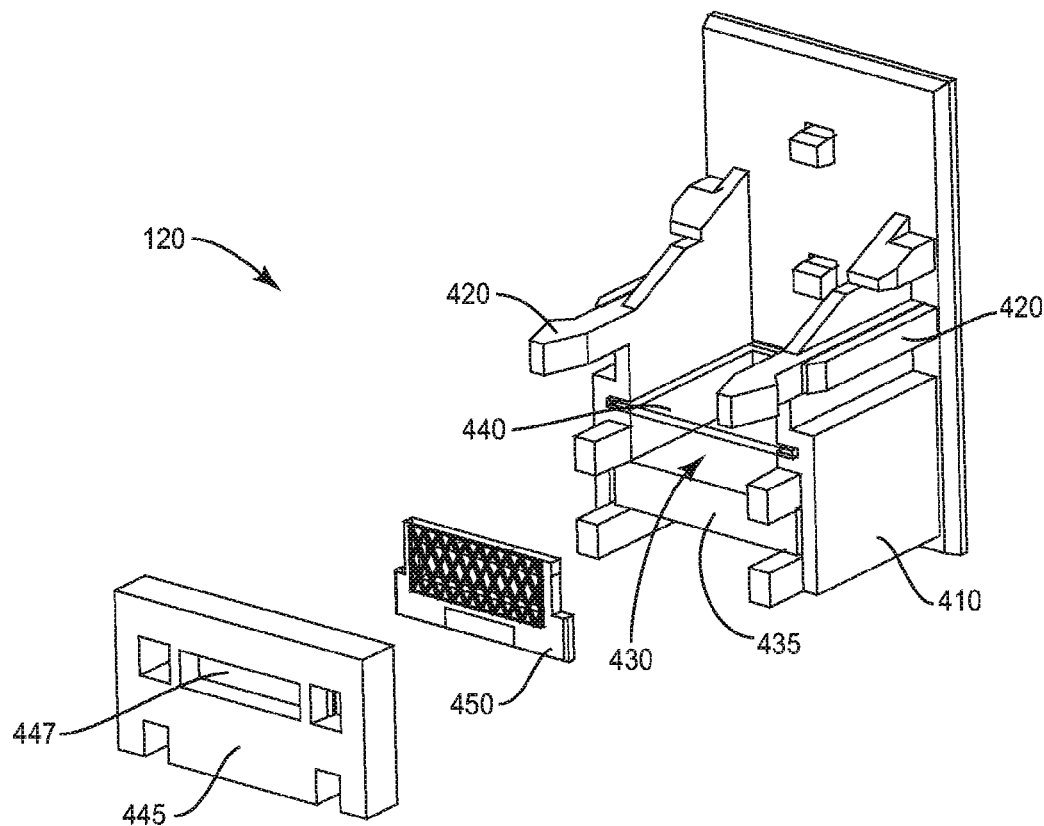
Figure 4D:
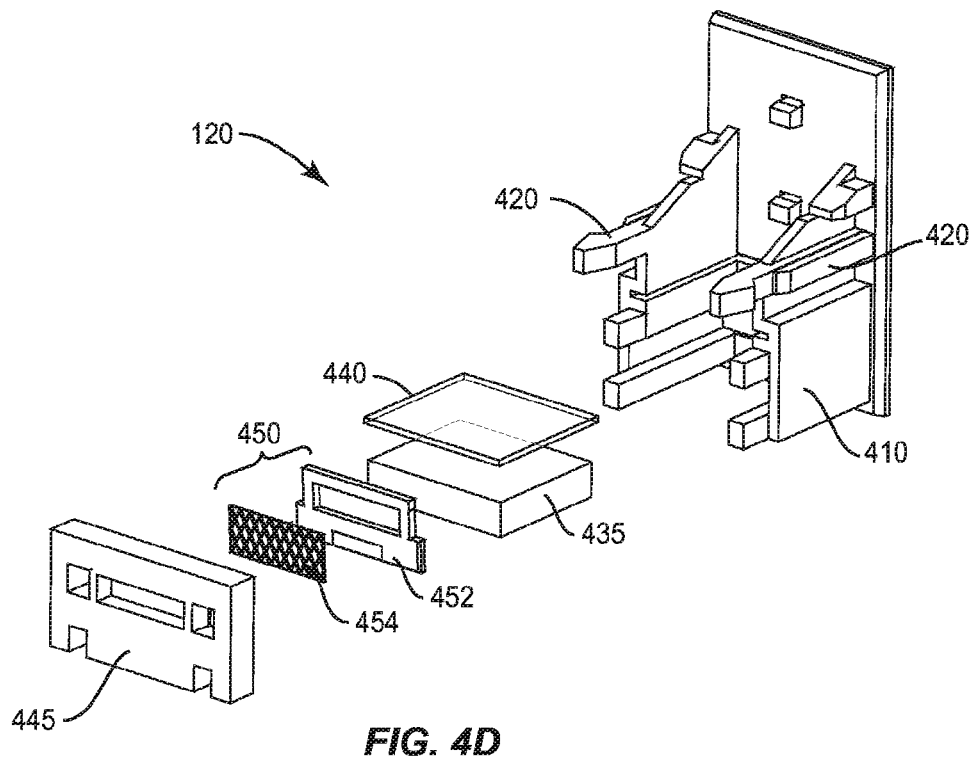

FIG. 1 provides an exterior view of an example automated insect monitoring system 100 that implements at least some of the features described above. FIG. 2 provides a cut-away view showing the interior of the same insect monitoring system 100. FIG. 3 provides a view of automated insect monitoring system 100 in which a removable chamber portion 120 has been removed from the main body, while FIGS. 4a, 4b, 4c, and 4d provided exploded views of the removable chamber portion 120.

As seen in FIGS. 1, 2, and 3, insect monitoring system 100 comprises a multi-part housing, including a main body 110 and a removable chamber portion 120, each of which may be made from inexpensive plastic materials, in some embodiments. In the illustrated example, a tab 140 is provided to allow the removable chamber 120 to be slid at least partly out of the main body 110, for inspection or replacement. In some embodiments, tab 140 must be manipulated in a particular direction to disengage a latching mechanism that retains the removable chamber 120 within the main body during normal use. The chamber portion 120 also includes a crevice 130, which is sized to allow an adult bedbug to enter an interior chamber within the removable chamber portion 120.

The main body 110 has an interior region 170, which may be used to house electronics, one or more batteries, etc. Batteries are not shown in the figures, but FIG. 2 does illustrate a circuit board 210, which carries a packaged multi-pixel optical sensor 230 and a lens assembly 220, as well as an electronics circuit 250, which in turn may comprise a processor, memory, and a communications circuit, in some embodiments.

The illustrated automated insect monitoring system 100 also includes a heating element 310 and a printed circuit 320 for carrying backlighting components. It will be appreciated that the heating element 310, as discussed in detail below, is optional, and thus may not appear in some embodiments. Further, as discussed below, the illumination in some monitoring system embodiments may be provided by means other than backlighting, in which case the printed circuit board 320 may not be present at all, or may be positioned elsewhere in the apparatus.

In some embodiments, the outer dimensions of the insect monitoring system 100 may be about 75 millimeters by 45 millimeters by 20 millimeters, for systems that are powered by two AA-sized batteries housed within the system package. Embodiments that receive external power or that use smaller batteries may be considerably smaller, e.g., having a reduced length. Some of these embodiments may have dimensions of about 30 millimeters by 45 millimeters by 20 millimeters. The interior dimensions of the photo chamber, which is described in more detail below, may have dimensions of about 10 millimeters by about 10 millimeters by about 5 to 30 millimeters, with the latter (height) dimension possibly depending on whether the interior chamber incorporates a "pitfall" element to prevent an intruding insect from climbing back through the entry crevice 130.

FIGS. 4A, 4B, 4C, and 4D provide exploded views of an example embodiment of a removable chamber portion 120. This example embodiment comprises a main cartridge body 410, which includes guide/retaining pins 420 to facilitate insertion and removal of the removable chamber portion 120 in the main body 110. In the illustrated embodiment, an interior chamber 430 is defined within: a removable, transparent, ceiling piece 440; a removable, translucent floor section 435; an end cap 445; and interior side walls of the main cartridge body 410. The ceiling piece 440 constrains vertical movement by an insect in the internal chamber 430, and is transparent to allow visual inspection of the internal chamber 430, when the removable chamber portion 120 is removed from the main body 110, as well as to provide visibility into the internal chamber 430 for the multi-pixel optical sensor 230. In the illustrated embodiment, the vertical position of the ceiling piece 440, relative to the floor section 435, keeps the insect confined within a narrow region, which minimizes the depth of field needed for the optical sensor 230. In some embodiments, as will be discussed in further detail below, the internal chamber 430 and any insects therein may be illuminated through the transparent ceiling piece 440 as well.

End cap 445 includes an opening 447 to allow air/gas flow through the interior chamber 430. A screen assembly 450, which comprises a filter frame 452 and a screen element 454, is retained against the main cartridge body 410 by the end cap 445, allowing air/gas flow but preventing any insects within the internal chamber 430 from escaping. In operation, heat generated by the electronics within the monitoring system 100 will flow through the opening 447, into the internal chamber 430, and out the crevice 130, providing a natural lure to bedbugs.

Notably, heat can act as an attractant (lure), arrestant, and repellant, for bedbugs, depending on the temperature. At temperatures close to human body temperature, e.g., at about 95 degrees Fahrenheit, air flowing or radiating out of the crevice 130 acts as an attractant for bedbugs. At higher temperatures, e.g., at temperatures above about 130 degrees Fahrenheit, air flowing or radiating out of the crevice 130 acts as a repellant. Within the interior chamber 430, air at temperatures above about 130 degrees Fahrenheit will serve as an arrestant, immobilizing most insects that have entered the chamber. Thus, in some embodiments, a heater can be selectively activated under microprocessor control, upon the detection of an insect intrusion into the interior chamber. This will serve to immobilize the insect, facilitating clearer imaging for classification purposes.

In some embodiments, as will be described in further detail below, gaseous attractants, arrestants, and repellants may also be controllably released within the monitoring system 100, and allowed to flow through the internal chamber 430 and out the crevice 130 in the same manner described above.

In some embodiments, the surface of floor section 435 may have a tacky substance on it, so as to capture an intruding insect and keep it relatively still for imaging purposes, as well as for subsequent analysis. This tacky substance may comprise a liquid applied to the floor section 435, or a tacky film applied to the floor section 435, etc.

Figure 5:
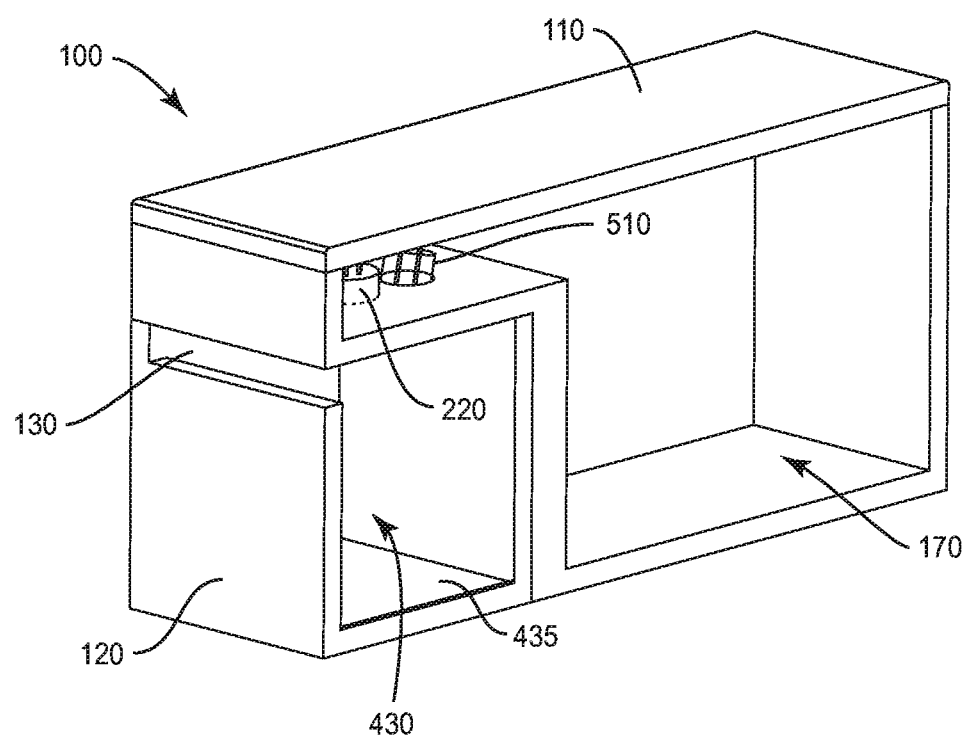
FIGS. 5, 6, 7, and 8 illustrate several schemes for illuminating an interior chamber of an insect monitoring system.
Figure 6:
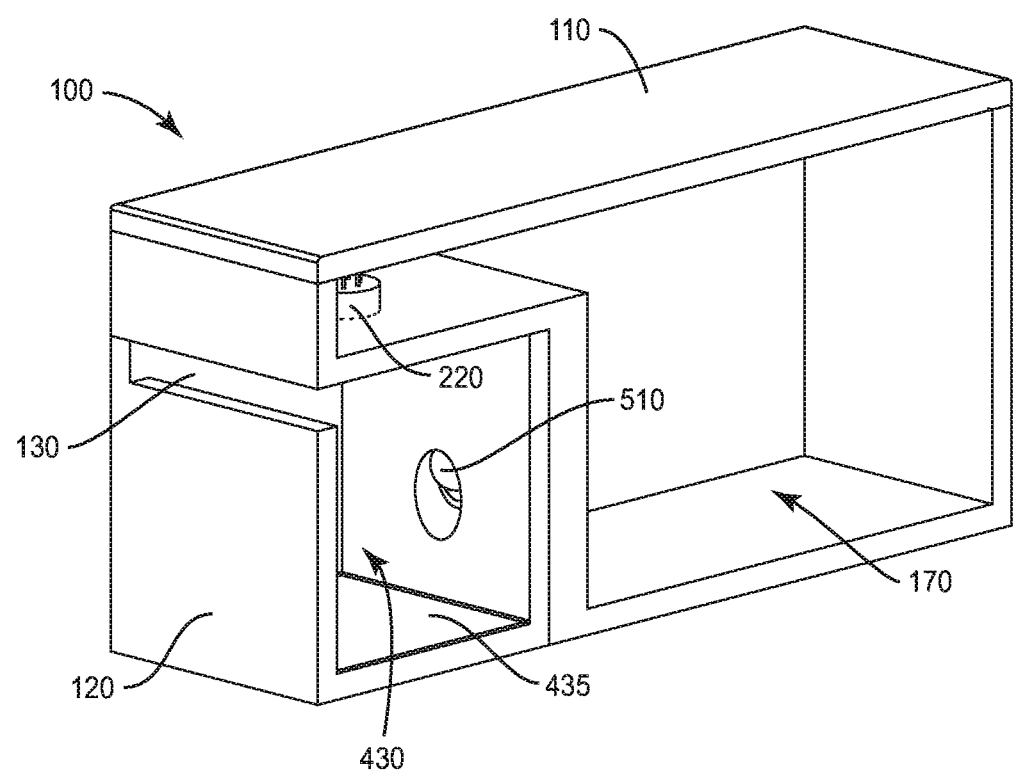

Insect monitoring system 100 further includes a light source arranged so that it illuminates at least a portion of the surface of floor section 435. The light source can be arranged in any of a variety of positions around the interior chamber 430. In some embodiments, such as in the simplified version of monitoring system 100 shown in FIG. 5, the light source is a single point source 510, such as a light-emitting diode (LED), positioned so that it illuminates the surface of floor section 435 from the opposite side of the interior chamber 430. In some embodiments, the light source may be positioned so that it illuminates the surface of floor section 435 from an angle (relative to the floor surface's perpendicular), as shown in FIG. 6, to generate shadows on the surface of floor section 435 from an insect or other object on the floor's surface. These shadows can be exploited by the image processing to enhance insect detection and/or identification. Of course, while only a single point light source is illustrated in these and several other embodiments, two or more point sources, e.g., LEDs, may be used in some embodiments, e.g., to provide more intense or more uniform illumination.

In other embodiments, the illumination of the floor section 435 is not provided by shining light through the interior chamber 430, but is instead provided from behind a transparent or translucent portion of the floor section 435.

Figure 7:
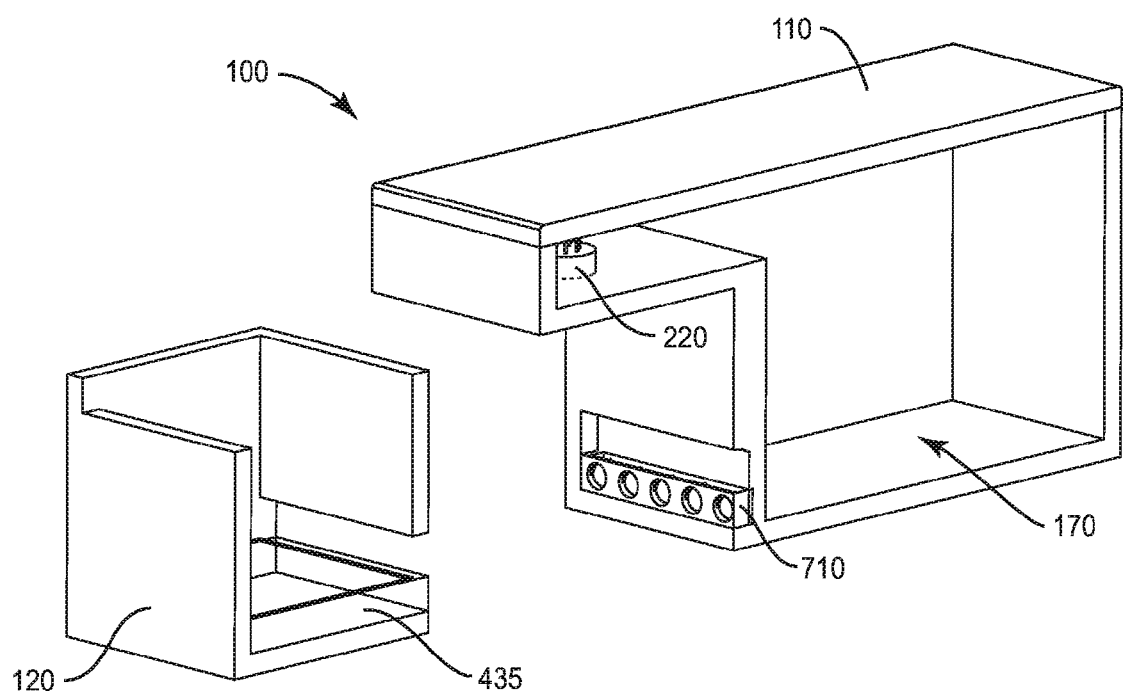
Figure 8:
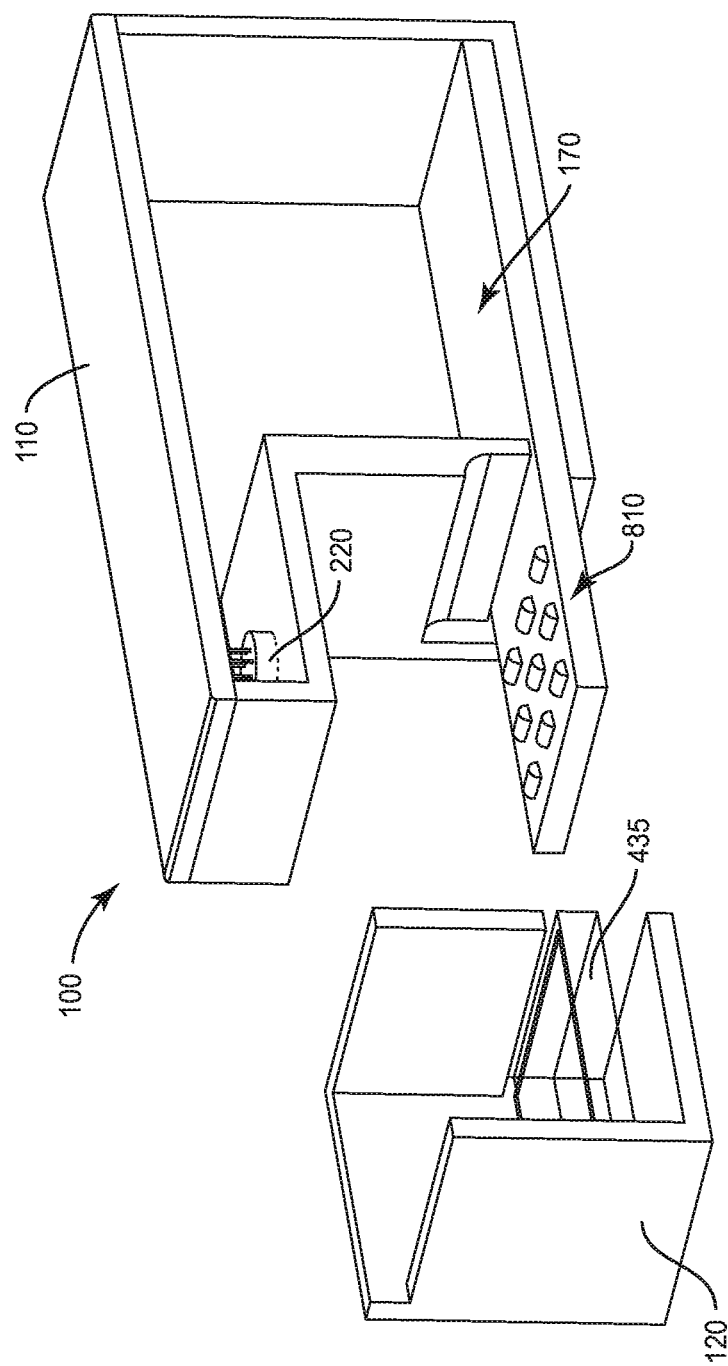

Examples of this approach are shown in FIGS. 7 and 8. The example in FIG. 7 shows an array of point light sources 710 (e.g., LEDs) that are affixed to the main body 110 and that directs light into the edge of the floor section 435, which in this case is adapted to act as an optical waveguide, e.g., a "light pipe," so as to illuminate the surface of the floor section 435. The floor section 435 receives the light from point light sources 710, diffuses it, and delivers it to the surface of the floor section 435. Inexpensive plastic light pipes are commonly used in handheld electronic devices, and are readily adaptable to the configuration shown in FIG. 7.

The example in FIG. 8 illustrates a different approach to illuminating the surface of floor section 435 from behind. With this approach, an array of point light sources 810 are affixed to a rigid surface that extends behind a transparent or translucent portion of the floor section 435. The floor section 435 in this case may act as a diffuser, or a separate diffuser may be positioned between the point light sources 810 and the floor section 435, to provide more uniform illumination of the surface. Again, inexpensive plastic light diffusers are well known and readily adaptable to configurations like those shown in FIG. 8.

Figure 15:
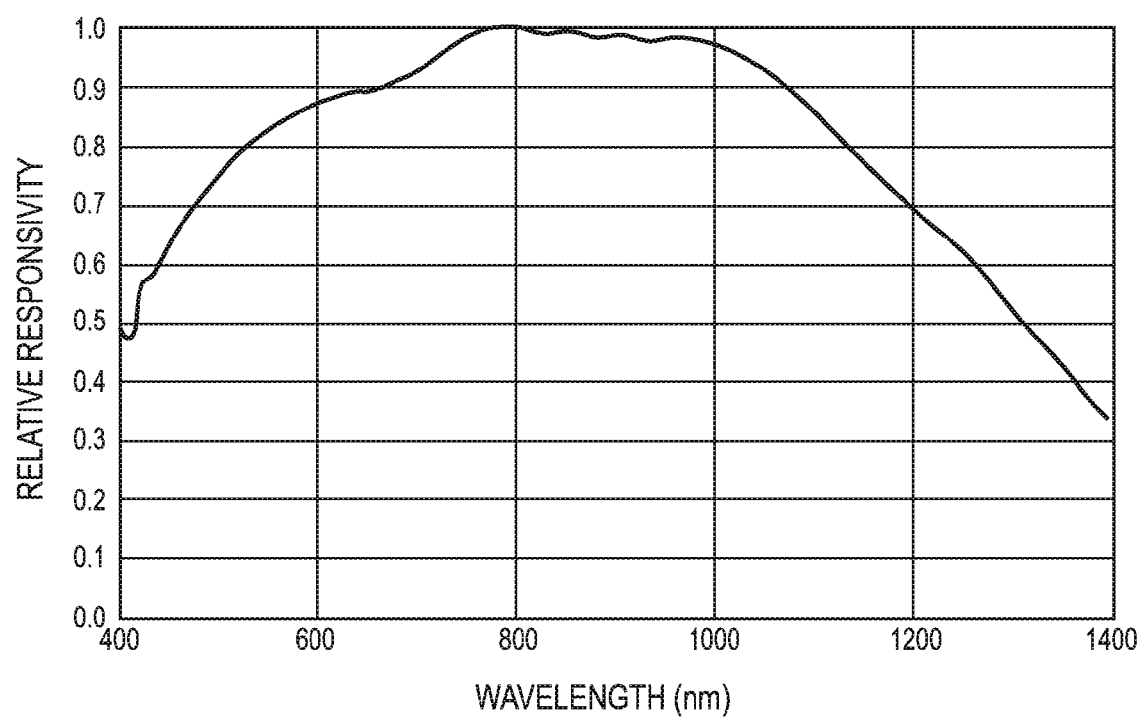
FIG. 15 shows an example responsivity curve for an infrared-tuned optical sensor.

The light source may emit visible or invisible light (e.g., infrared), in various embodiments. Infrared light may be particularly advantageous in some embodiments, for several reasons. For example, if the input or output of the optical sensor 230 is tuned (e.g., through optical filtering, digital filtering, or other means) so that the resulting image data reflects a sensitivity to infrared light but less sensitivity to visible light, then the system will be less sensitive to variations in ambient light that may leak through the crevice 130 to the interior chamber 430. Further, infrared light is expected to be a lure for bedbugs—as a result, infrared illumination leaking from inside the chamber portion 120 to the outside of the device may attract bedbugs to the interior chamber 435. FIG. 15 illustrates an example responsivity curve for a near-infrared-tuned CMOS optical sensor, where relative responsivity is plotted against the received light's wavelength.

With the approaches shown in FIGS. 7 and 8, and with variants of those approaches, an insect on the surface of floor section 435 is illuminated from behind (with respect to the optical sensor 230), presenting the optical sensor 230 with a silhouette view of the insect. While these approaches do not illuminate those surface details of the insect that face the optical sensor 230, they do have the advantage of facilitating the collection of very high-contrast images. They also have the potential to illuminate an insect's internal features, which may facilitate detection and classification, including a means to estimate how recently the insect fed. Note that a backlighting approach like those shown in FIGS. 7 and 8 may be combined with a front-lighting approach like that shown in FIGS. 5 and 6, in some embodiments. In some of these embodiments, the lighting from behind the floor section 435 and from above the floor section 435 may occupy different parts of the electromagnetic spectrum, to facilitate more sophisticated image processing and improved identification and/or classification of insects that intrude into the interior chamber 430.

In each of these example embodiments discussed above, insect monitoring system 100 also includes a multi-pixel optical sensor 230, which is arranged within the housing so that the sensor's field of view covers a substantial portion of the surface of floor section 435. As a result of this configuration, each of the multiple pixels of the optical sensor 230 corresponds to, i.e., can be mapped to, a segment of the floor surface. In the illustrated embodiments, the optical sensor 230 is arranged so that it is directly opposite the surface of the floor section 435 so as to have a head-on view of the floor section's surface. It will be appreciated, however, that the optical sensor 230 may be arranged at any of several other points around the interior chamber, e.g., so that it has an angled view of the surface of floor section 435, so long as the sensor's field of view encompasses a substantial part of the floor section's surface.

In the illustrated embodiments described above, the chamber portion 120 is designed so that it can be at least partly separated from the main body 110 of the housing, to allow visual inspection of the interior chamber 430. This was shown in FIG. 3, which illustrates an embodiment in which the chamber portion 120 can be completely separated from the main body 110. It will be appreciated that chamber 120 and main body 110 can be designed with any of a wide variety of retaining features to allow the two pieces to be "snapped" together and apart, without damage to either part. In other embodiments, the main body 110 and chamber portion 120 may be designed so that the chamber portion 120 can be separated from the main body 110 to a sufficient extent to allow visual inspection of the floor surface, while still remaining attached to the main body 110.

In some embodiments, the system is designed so that some or all of the light source, optical sensor 230, and electronics remain affixed to the main body 110 when the chamber portion 120 is removed. With some of these embodiments, the chamber portion 120 may be treated as a disposable part—once it is contaminated with a captured insect or insects, it can be removed and replaced with an inexpensive replacement piece.

Figure 9B:
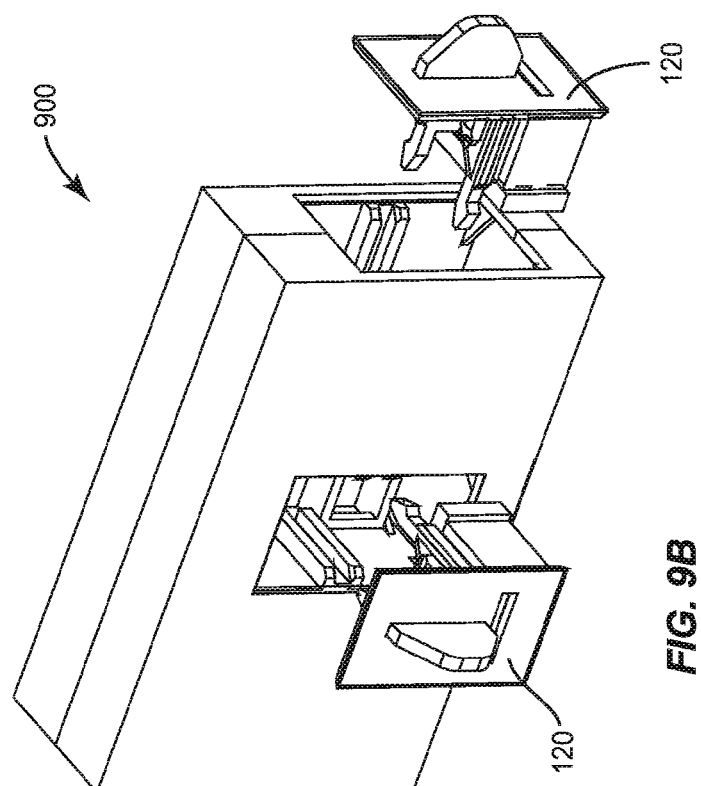
FIGS. 9A and 9B illustrate a triple-entry insect monitoring system.
Figure 9A:
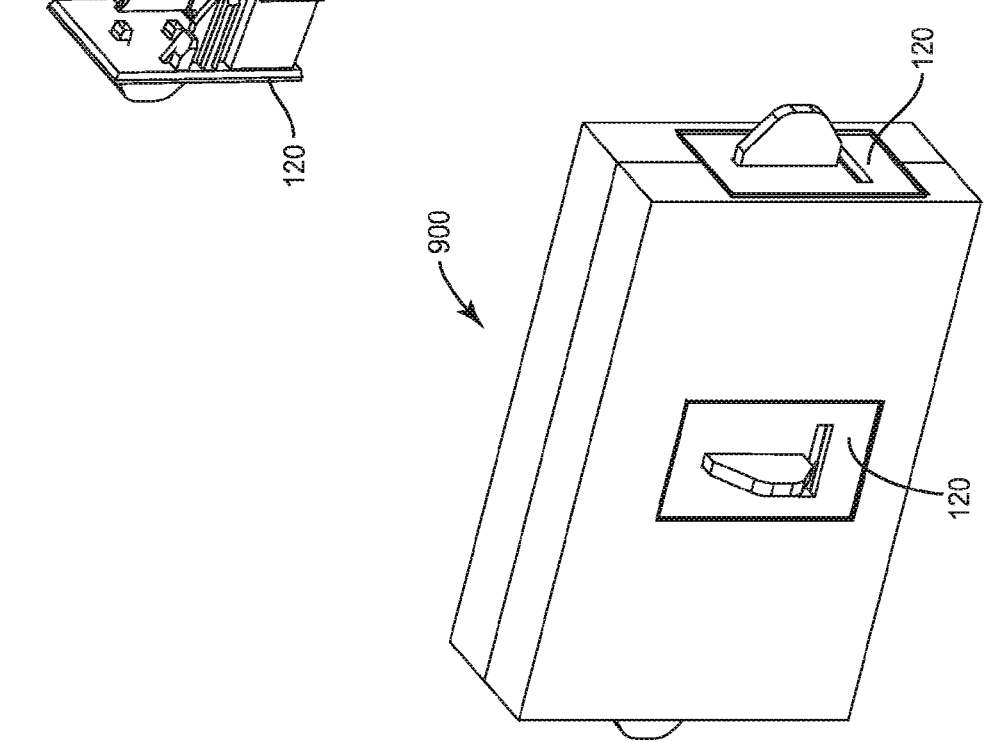

Some embodiments may be equipped with multiple entry points and/or multiple removable chamber portions 120. One such embodiment is illustrated in FIGS. 9A and 9B, which show a triple-entry automated insect monitoring system 900 with three removable chamber portions 120. A double-entry system might simply omit one of the chamber portions from the configuration shown in FIGS. 9A and 9B, for example. Other configurations with even more than three entry points and/or removable chamber portions 120 are possible.

As noted above, the multi-pixel optical sensor used to obtain an image of the floor surface and any insect situated on it is a relatively low-resolution sensor, in some embodiments, with a number of pixels ranging from at least four to as many as about 1000. Some embodiments may use a sensor with 22×22 pixels, for example, for a total of 484 pixels. In an example embodiment, the imaged surface, corresponding to the majority of the surface of floor section 435, is about 10 millimeters by 10 millimeters. Thus, each pixel maps to approximately 0.45 mm×0.45 mm on the floor, which provides enough resolution to detect and classify insects using the various algorithms discussed herein. A smaller number of pixels may be suitable for embodiments in which only detection of an intruding insect is needed. In embodiments where classification of the insect is desired, more pixels and a higher resolution are needed, so that the smallest insect that is anticipated to be imaged occupies enough pixels in a captured image for the appropriate processing to be carried out. For bedbug detection, for example, the image sensor may be arranged, relative to the imaged floor surface, so that each pixel corresponds to no more than about 0.5 millimeters square, in some embodiments, to ensure that the smallest bedbug is likely to be "seen" by several pixels.

Requirements for a lens will depend on the placement of the multi-pixel optical sensor, relative to the internal chamber. To obtain focus and magnification at a distance of about 25 millimeters, for example, a lens with a focal length of 2.33 millimeters is used.

The electronics shown in the embodiments illustrated above include a processing circuit (in electronics circuit 250) configured to receive optical data from the multi-pixel optical sensor, to analyze the optical data to detect the intrusion of an insect or other object into the interior chamber 430 by comparing recently received optical data to previously received optical data. A difference between the recent data and the previous data, if significant enough, indicates that something has moved into the image field. In some embodiments, the processing circuit then generates an indication in response to detecting the intrusion of the insect or other object into the interior chamber. In some simple embodiments, this indication is simply an indication that an intrusion has been detected. In other embodiments, the difference-based detection described above triggers further processing to refine the detection decision, e.g., to reduce false alarms, and/or to attempt a classification of the intruding object. The processing circuit includes, in an exemplary embodiment, a microprocessor and associated memory as well as a communications circuit. The memory stores program instructions, e.g., in flash memory or other nonvolatile memory, for execution by the microprocessor to carry out one or more of the several methods described herein. The memory also includes working memory, such as random-access memory (RAM) or other volatile or non-volatile memory, for use by the microprocessor in carrying out these methods and/or for communicating through the communications circuit.

Figure 10A:
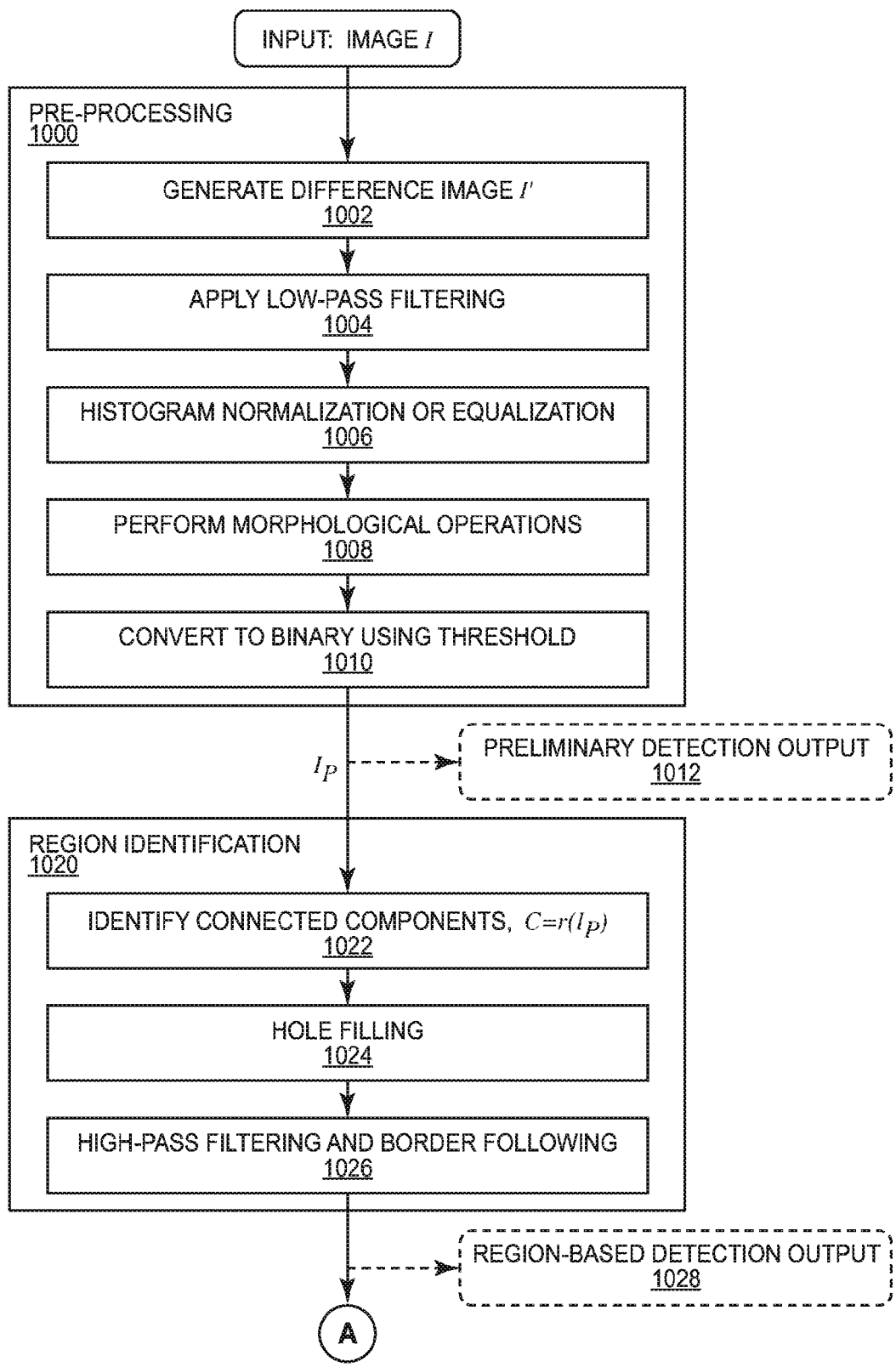
FIGS. 10A and 10B are process flow diagrams illustrating an example image processing algorithm.
Figure 10B:
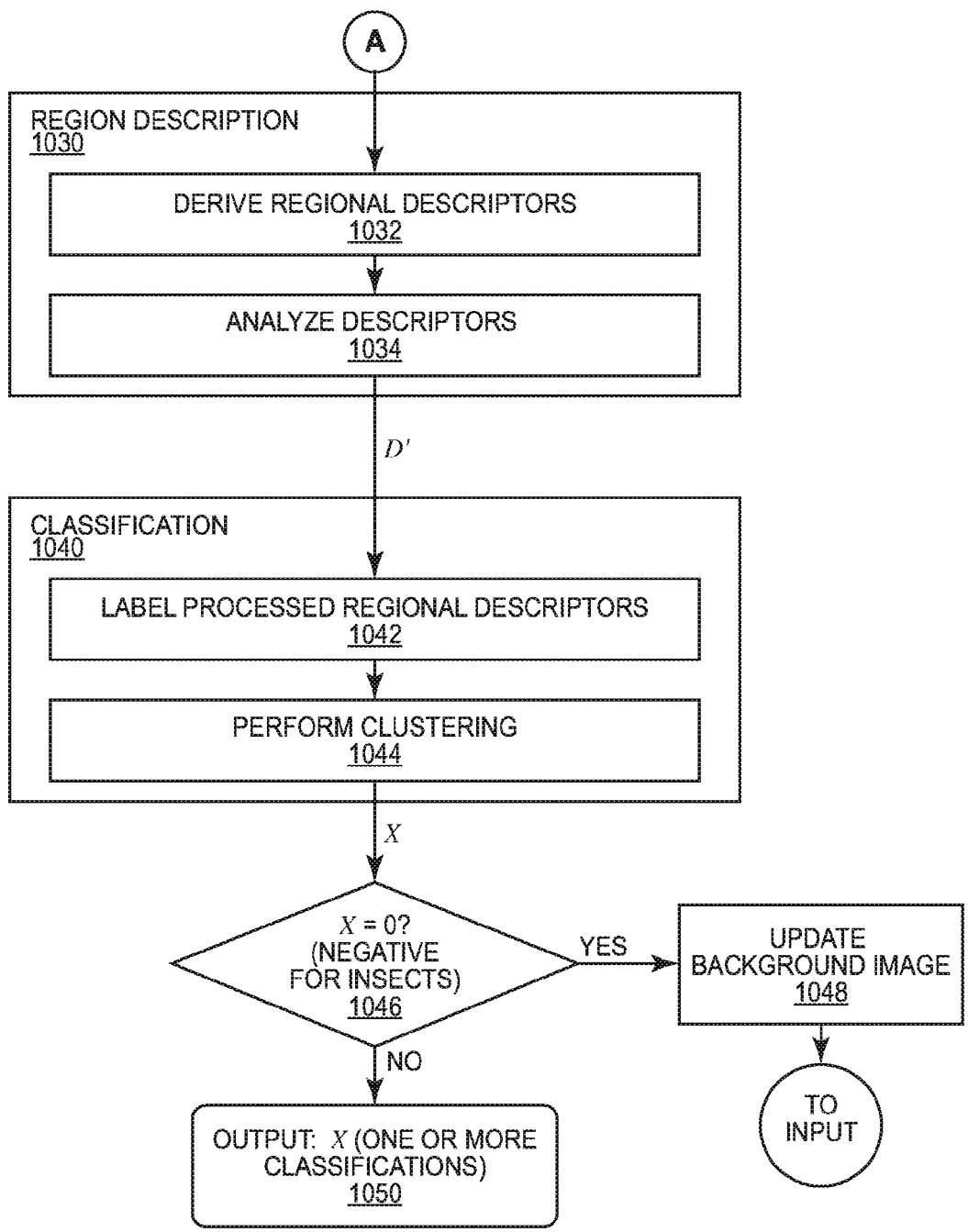

FIG. 10 illustrates a process flow diagram illustrating a detection and classification algorithm that might be used in some embodiments. It will be appreciated that some embodiments might use only the detection portion of the illustrated algorithm, while others may use variations of the exemplary image processing and insect classification techniques illustrated in FIGS. 10A and 10B.

The input to the process flow shown in FIG. 10A is a multi-pixel image I obtained from the optical sensor 230. The image data, I, is first provided to a pre-processing stage 1000. This stage includes a background subtraction operation, 1002, which generates a difference image I' as a function of image I and a background image B. As will be discussed in further detail below, the background image B is derived from at least one previous image, e.g., from a weighted average of previous images from the optical sensor. Subtracting the background image increases the contrast of the processed image and removes artifacts in the image I that may be caused by dust, burnt-out pixels, etc.

As shown at blocks 1004, 1006, and 1008, the difference image I' is subjected to one or more of a low-pass filtering function g(I'), histogram normalization or equalization function n(I'), and/or one or more morphological operations m(I'). The most basic morphological operations are erosion and dilation. Erosion contracts or deflates a region of pixels by decreasing the value of the boundary pixels. Dilation expands or inflates a region of pixels by increasing the value of the boundary pixels. Morphological opening is the dilation of an eroded image, and morphological closing is the erosion of a dilated image. Note that any one or more of these operations might be omitted, in various embodiments. Finally, as shown at block 1010, the processed image data is made binary by comparing pixel values to a global or local threshold. This process may be global, e.g., comparing every pixel to the same value, or local, e.g., comparing each pixel to a value that is calculated using the values of its neighboring pixels.

In any case, the output of the pre-processing stage 1000 is a preliminary detection output, as shown at block 1012. This output is positive, indicating at least the possibility of a detected insect, if the sum of the processed pixel intensities in the entire image area or in a localized region is greater than an empirically determined threshold, and negative otherwise. In some embodiments, the image processing may stop here, and the preliminary detection output is reported. In others, this preliminary detection output instead serves as a trigger for further processing.

In the process flow illustrated in FIG. 10A, however, the preliminary detection output triggers further processing of the image data, including a region identification sub-process 1020. This sub-process includes, as shown at block 1022, the step of identifying a set of connected components in the processed pixel data, i.e., identifying connected components $C=r(I_P)$, where C is the set of connected components, $I_P$ is the processed pixel data, and r(*) is the region-growing function. Connected components may be found using a region-growing or contour retrieval function. Region growing involves searching the neighborhood of a seed pixel for other pixels of the same value until, continuing until no more pixels of the same value are found. Retrieving image contours generally involves high-pass filtering followed by border following, as shown at block 1026. Prior to this step, a hole-filling algorithm may be employed to fill in the translucent stomachs of the unfed insects, as shown at block 1024. Hole filling could be achieved through morphological closing or a similar technique.

In some embodiments, each of the identified connected components (as processed by the high-pass filter and hole-filling functions, as applicable) is evaluated to determine whether there is a connected component that exceeds a particular size. As shown at block 1028, these embodiments may provide a region-based detection output, based on this evaluation, that is positive for intrusion detection in the event that the size (i.e., area) of any connected component is greater than an empirically derived threshold value, and negative otherwise. This region-based detection output may be reported (as discussed in further detail below) in some embodiments, or may simply serve as a trigger for a classification sub-process, in others.

Continuing from the process flow shown in FIG. 10A, FIG. 10B illustrates a region description sub-process 1030. As shown at block 1032, this sub-process derives one or more regional descriptors corresponding to each of one or more regions in a connected component C', e.g., according to a function D=q(C'), where D is the set of regional descriptors, C' are the processed connected components derived from the image data according to the steps shown in region-identification sub-process 1020, and q(*) is a function that quantifies the descriptors D. Region description sub-process 1030 may further comprise an analysis step that analyzes the descriptors, using techniques such as principal components analysis (PCA), providing an output D'=a(D), where a(*) is a function that analyzes the descriptors D. This is shown at block 1034.

The output from region-description sub-process 1030 is provided to a classification sub-process 1040. Here, as shown at block 1042, the processed regional descriptors D' are labelled based on their likeness to each of a set of possible classifications. In some embodiments, clustering may be employed, as shown at block 1044, to compare the descriptors D' to the descriptors for common insect variants.

The output of the classification sub-process 1040 can be formulated as X=s(D'), where X is a set of classifications (which may be binary) for each region and s(*) is a classification function. X may consist of a binary determination of whether or not the intruder belongs to a certain class of insect, e.g. bedbugs, or may differentiate among a number of insect classes, e.g. bedbugs, ants, roaches, etc.

The results of the classification sub-process can be used to determine whether an intruder is present at all and/or to identify a type of intruder. The results, if negative, can also be used to update the background image, to improve subsequent processing. As shown at blocks 1046 and 1048, a classification result of X==0, i.e., a classification result that is negative for insects of any type, results in an updating of the background image used in subsequent processing, as shown at block 1048. This may be done according to a function N=k(I', B), where k(*) is a temporal filter to incorporate the new image into the background image. After the background image is updated, the image processing shown in FIGS. 10A and 10B may be repeated, using a new image I.

If the classification result indicates that an insect was detected, on the other hand, the output indicates the classification or set of classifications that apply to the analyzed image, as shown at block 1050. This may specify a particular type of insect or a life-stage for a particular type of insect, in some embodiments. Note that in some embodiments and in some circumstances, this classification result may indicate that while an insect was detected, no classification was possible.

Figure 11:
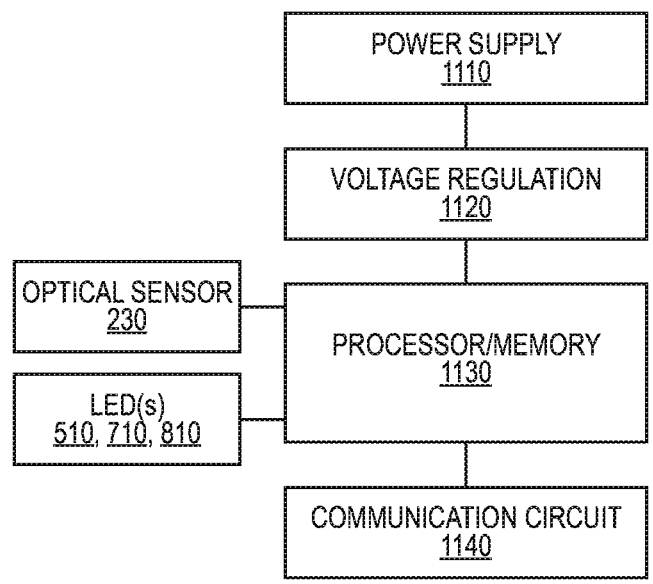
FIG. 11 is a schematic diagram illustrating electrical components of an example insect monitoring system.

FIG. 11 is a schematic diagram illustrating the electronics included in some embodiments of the insect monitoring systems described herein. These electronics consist of three major subsections: power, processing, and communications. The power supply circuit 1110 has a modular design, in some embodiments, allowing the design to be changed to best fit a specific market. In some embodiments, the power supply circuit 1110 interfaces to AC power provided from a wall outlet, while in others it is powered by one or more batteries, e.g., a pair of conventional AA batteries. It will be appreciated that the details of the power circuit 1110 will vary, depending on the input and the specific requirements, but it will be further appreciated that various circuit designs for a wide range of inputs and performance requirements are well known.

The illustrated example circuit further shows a voltage regulation circuit 1120, which operates to bring the voltage down to an operating level for powering the optical sensor 230, LEDs 510, 710, and 810 processor/memory circuit 1130, and communication circuit 1140. An appropriate output voltage for the voltage regulation circuit 1120 may be 1.8 volts, for example, although other voltages are possible. Again, designs and components for providing the necessary performance of voltage regulation circuit 1120 are well known.

Processor/memory circuit 1130 can either be standalone or contained within an applications-specific integrated circuit (ASIC) that also comprises the communications circuit 1140. The processor/memory circuit 1130 comprises one or more microprocessors, microcontrollers, digital signal processors, or the like, coupled to memory that stores program instructions for carrying out control of the insect monitoring system and for carrying out any of the image processing techniques described above. The communications circuit 1140 is configured to support at least one wireless communications technology, preferably (although not necessarily) according to an industry standard protocol, such as Bluetooth®, Wi-Fi, etc.

The processor/memory circuit 1130 reads pixels from the multi-pixel optical sensor 230 to generate an image, and then applies one or more of the above-described algorithms, or variants thereof, to detect insect intruders and/or classify the intruding insects. Using general purpose I/O pins, the processor/memory circuit 1130 can toggle the LED(s) as necessary, e.g., to provide constant illumination or flashing illumination, etc. Upon obtaining a detection and/or classification result, the processor/memory circuit 1130 sends a message to a remote device, the device carrying an indication that an insect has been detected. Any or all of the detection and/or classification results may be forwarded as part of this message, or in response to a query received from the remote device. In some embodiments, no image data is forwarded to the remote device. In other embodiments, image data is forwarded along with the detection/classification indication. In still others, image data associated with a detection/classification event may be stored in memory, and subsequently forwarded to a remote device in response to a specific inquiry.

In some embodiments, the communications circuit 1140 is also designed for modularity, so that the specifics of the supported communications link can be changed to best suit a specific market. Circuits supporting Bluetooth Smart®, ANT+, and Wi-Fi are currently available and may be suitable for various applications of the insect monitoring system. Each has its own drawbacks and benefits; power consumption, the availability of email alerts, phone connectivity, and network privacy are all considerations.

While the use of chemicals may be unnecessary or undesirable in applications, some variants of the insect monitoring systems described above contain a means to dispense chemical compounds, such as attractants, repellants and arrestants. These compounds may be synthetic or natural pheromones, kairomones, essential oils, etc. They may also be in liquid, solid, and vapor states. Additionally, they may be suspended in a gel. They may also be contained in vessels or wrappers with one or more apertures, including porous membranes, to limit the outflow. A space in the lower portion of the monitoring system is designed to receive and store these compounds, which may be provided in removable and replaceable packaging.

FIGS. 12A and 12B illustrate an example insect monitoring system 1200 that is adapted to contain two chemical containers 1210, each holding a chemical 1215 (in liquid, solid, or gel form). While two containers 1210 are shown in FIGS. 12A and 12B, it will be appreciated that a single container 1210 may be used, in some embodiments.

The vapors that emanate from the packaged chemical compounds may be channeled through each of the interior chambers 430 (i.e., the "photo booth") of the monitoring system, by departing the storage vessels, passing through a plenum into the interior chamber 430 and then entering the photo booth via a screen. See, for example, FIGS. 4A-4D, which illustrates details of an end cap 445, opening 447, and screen 454, which may be used to allow chemical vapors into the interior chamber 430 of a chamber portion 120. In some embodiments, a plenum may be installed between the chemical container 1210 and the opening 447 in end cap 445, to route the vapors towards and into the interior chamber 430. Vapors may then linger within the interior chamber 430 or exit the photo booth through the crevice 130. Attractant vapors that leave the photo booth will likely create an intensity gradient that decreases as it radiates; the attractant vapors lure the insects and this intensity gradient can be used by insects to converge on the photo booth.

Unlike other traps, which require specific attractant, arrestant or repellant compounds, the disclosed monitoring system can be compound-agnostic. The disclosed monitoring system is designed to accommodate any chemical compound that an end-user wishes to employ. Further, these chemicals may be automatically dispensed, under the control of the onboard processing circuits, using a motor 1220, separately controllable spring-loaded valves 1230, and a rotating cam 1240, which is attached to the motor 1220 and can be rotated, under processor control, to separately actuate each of the spring-loaded valves 1230. Note that one or more solenoids or other electromechanical devices can be used as an actuator, in various embodiments.

Thus, for example, the processing circuit may be configured to open one of the spring-loaded valves 1230, whether periodically or for an extended interval, to release an attractant vapor from one of the containers 1215. Upon detection of an insect in one of the interior chambers 430, the processing circuit may then control the motor 1220 to rotate the cam 1240 so as to allow the first spring-loaded valve 1230 to close and so as to open the other spring-loaded valve 1230, allowing an arrestant vapor to emanate from the other container 1215. After a predetermined interval, the processing circuit may then rotate the cam 1240 again, so as to allow both spring-loaded valves to close, e.g., until the unit is reset, either by human interaction (e.g., by the pushing of a reset button) or by a reset command received via the onboard wireless communication circuit.

As shown in the example embodiment in FIG. 12, then, an electronic means of controllably dispensing compounds is provided in some embodiments of the automatic insect monitoring systems. While some passive dispensers may yield predictable dispersion levels, none can controllably vary them. The system shown in FIG. 12 is an example of a programmable system that is not only agnostic to the compounds it dispenses, but can vary both the dispersion levels and intervals. This enables variable dispensation of attractants, arrestants and repellents. It also enables schedule- and/or event-driven dispensation.

Furthermore, it enables open- and closed-loop control which can be user-defined, to modify variables that impact trap performance, or adapt to external factors including regional biases, environmental conditions, species-specific preferences and strain-specific proclivities. An actuator, such as the rotating cam 1240 in FIG. 12, is designed to open and seal the apertures through a valve, such as the spring-loaded valve 1230 shown in FIG. 12, which allows vapors to flow from the storage vessels into the plenum, through the photo booth and to the exterior of the insect monitoring system. This actuator may be programmed to open the apertures to a full- or partial-level, which is one way of managing flux impedance. This actuator may alternatively or also be programmed to open and seal the vessel apertures according to a schedule, or event. An example of a schedule may include dispensing attractants nightly at or around midnight so as to attract bedbugs that, through nocturnal rhythms, will begin their active state. An example of an event may include the detection of a pest, which may trigger the actuator to open the arrestant compound so as to trap the insect. A chemical sensor may also be utilized, in some embodiments, to provide feedback to the trap's controller. This closed-loop approach will measure and report the intensities of the attractant, arrestant and/or repellants, either directly or through indicators, and permit the controller software to regulate the dispensation, and compensate for changing conditions such as ambient temperature, humidity, airflow, etc. When used in concert with the heat flowing through the interior chamber and to the exterior of the monitoring system, which is also controllable in some embodiments, a monitoring system may be tuned to serve as optimal lures for insects. Such regulation may also permit maximizing the endurance of compounds. No insect trap on the market currently provides this level of flexibility.

Figure 13:
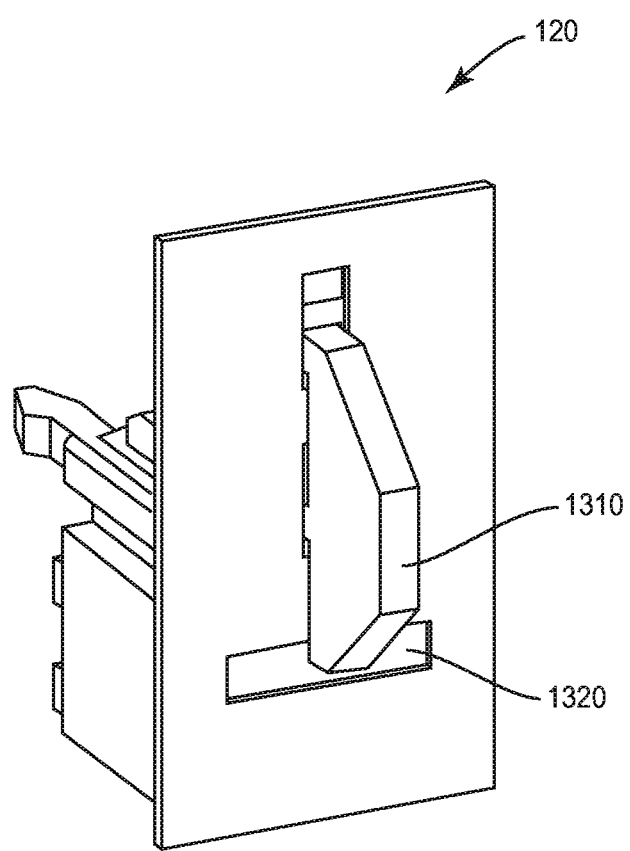
FIG. 13 illustrates details of another example removable chamber portion.

In some embodiments, a means of controllably closing the crevice 130 is provided. A manual means of controllably closing the crevice is shown in FIG. 13, which shows a removable chamber 120 in which a tab 1310 is used to open and close a door 1320 in the crevice 130. Specifically, in this example, an end-user may move the drawer's tab vertically to correspondingly move a barrier that obstructs the crevice. This traps the insect inside the photo booth, which is useful for observation and handling. In some embodiments, moving the tab 1310 in the opposite direction may engage a latching mechanism in the interior of the insect monitoring system, to retain the removable chamber 120 within the system.

An automated mechanism for closing the crevice 130 may also be used, in some embodiments. A plethora of mechanical transmission methods may be employed to automatically close the crevice door. One approach, illustrated in FIGS. 12A and 12B, includes the use of a servo-driven cam 1240 that moves one end of a lever arm 1250, causing the other end of the lever arm 1250 to move the crevice door. This actuated solution may be automatic, predicated on an event like the detection of an insect. Or, it may be triggered by a user, whether remotely or in proximity, e.g., through an electronic message.

Figure 14:
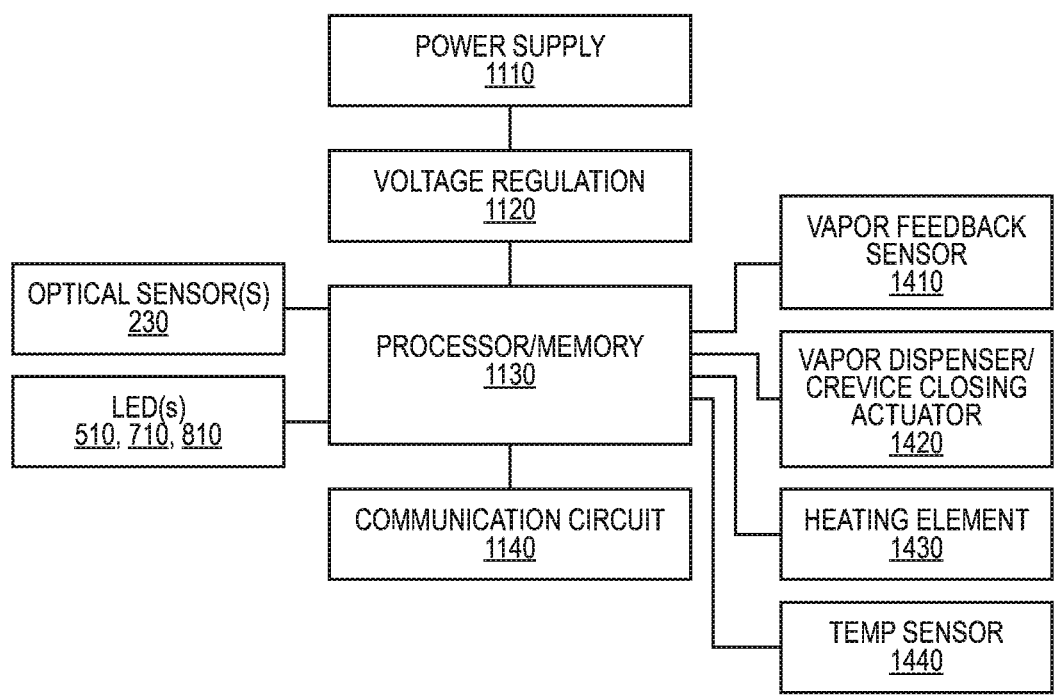
FIG. 14 is another schematic diagram illustrating electrical components of an example insect monitoring system.

FIG. 14 is a schematic diagram illustrating the electronic and electromechanical components of a more fully-featured version of the insect monitoring systems described herein. Like the schematic diagram of FIG. 11, the diagram of FIG. 14 illustrates a power supply 1110, a voltage regulation circuit 1120, a processor/memory circuit 1130, and a communication circuit 1140, as well as optical sensor(s) 230 and LED(s) 510, 710, 810. Unlike the schematic diagram of FIG. 11, the schematic of FIG. 14 includes a vapor feedback sensor 1410 and a vapor-dispenser/crevice-closing actuator 1420, a heating element 1430, and temperature sensor 1440. As discussed above, vapor feedback sensor 1410 can be used to provide closed-loop control of the vapor-dispensing mechanism driven by actuator 1420. Heating element 1430 can be automatically controlled, e.g., using feedback from temperature sensor 1440, to provide warm air flow into and through the photo booth chambers of the insect monitoring system; in some embodiments, the temperature can be controlled selectively, so that the air flow acts as a lure until an insect is detected, at which time the air temperature may be increased to act as an arrestant.

Several embodiments of an inventive insect monitoring system have been described above. The described insect monitoring systems provide a safe, effective, and inexpensive solution for automatically monitoring dwelling spaces for the presence of insects, and provide rapid notification of any detected infestations. It is to be understood that the invention(s) is/are not to be limited to the specific embodiments disclosed and that modifications and other embodiments are intended to be included within the scope of this disclosure. Although specific terms may be employed herein, they are used in a generic and descriptive sense only and not for purposes of limitation.

What is claimed is:

1. An automated insect monitoring system, comprising:
   a housing;
   an interior chamber within the housing, the interior chamber having a floor with a floor surface;
   a crevice providing access to the interior chamber from outside the automated insect monitoring system;
   a light source arranged within the housing to illuminate, at least intermittently, at least a portion of the floor surface;
   a multi-pixel optical sensor arranged within the housing so that multiple pixels of the optical sensor each correspond to a unique segment of the floor surface within a field of view of the multi-pixel optical sensor; and
   a processing circuit arranged within the housing and configured to receive optical data from the multi-pixel optical sensor, to analyze the optical data to detect the intrusion of an insect or other object into the interior chamber by comparing most recently received optical data to previously received optical data, and to generate an indication in response to detecting the intrusion of the insect or other object into the interior chamber.

2. The automated insect monitoring system of claim 1, wherein the light source is arranged to shine light onto the floor surface across at least a portion of the interior chamber.

3. The automated insect monitoring system of claim 2, wherein the light source is arranged to shine light onto the floor surface at an angle, relative to the floor surface and its perpendicular, so that an object on the floor surface casts a shadow on the floor.

4. The automated insect monitoring system of claim 1, wherein the light source is arranged outside the interior chamber and arranged so as to illuminate the portion of the floor surface from behind a transparent or translucent section of the floor.

5. The automated insect monitoring system of claim 4, wherein the light source is arranged behind the transparent or translucent section of the floor.

6. The automated insect monitoring system of claim 5, wherein the light source comprises a plurality of light emitting diodes arranged behind the transparent or translucent section of the floor.

7. The automated insect monitoring system of claim 4, wherein an output of the light source is coupled to the transparent or translucent section of the floor with an optical waveguide.

8. The automated insect monitoring system of claim 1, wherein the multi-pixel optical sensor has at least four but no more than about 1000 pixels.

9. The automated insect monitoring system of claim 1, wherein the optical sensor is arranged, relative to the floor surface, so that at least a majority of the unique segments of the floor surface corresponding to the pixels of the multi-pixel optical sensor have a surface area of no more than about 0.5 square millimeters.

10. The automated insect monitoring system of claim 9, wherein the optical sensor is arranged, relative to the floor surface, so that at least a majority of the unique segments of the floor surface corresponding to the pixels of the multi-pixel optical sensor have a surface area of no less than about 0.1 square millimeters.

11. The automated insect monitoring system of claim 1, wherein the floor surface comprises a tacky substance.

12. The automated insect monitoring system of claim 1, wherein the floor surface forms part of a removable chamber, configured so that the removable chamber can be separated from a main body of the housing for visual inspection of the floor surface, without damage to the removable chamber or the main body of the housing, while leaving the multi-pixel optical sensor in the main body of the housing.

13. The automated insect monitoring system of claim 1, wherein the floor surface forms part of a chamber that is arranged within the housing so that the chamber can be partially, but not completely, separated from a main body of the housing for visual inspection of the floor surface, without damage to the chamber or the main body of the housing, while leaving the multi-pixel optical sensor in the main body of the housing.

14. The automated insect monitoring system of claim 1, further comprising a wireless communication circuit, and wherein the processing circuit is configured to send a message via the wireless communication circuit in response to the generated indication, the message indicating that an insect intrusion has been detected and/or or indicating a classification of a detected insect or indicating both that an insect intrusion has been detected and a classification of a detected insect.

15. The automated insect monitoring system of claim 1, further comprising a power supply circuit arranged within the housing and configured to provide power to the light source, multi-pixel optical sensor, and processing circuit, from one or more batteries.

16. The automated insect monitoring system of claim 1, further comprising:
   one or more additional interior chambers, each with a corresponding crevice providing access to the additional interior chamber;
   an additional light source corresponding to each of the one or more additional interior chambers and arranged to illuminate at least a portion of a floor surface of the corresponding additional interior chamber; and
   an additional multi-pixel optical sensor corresponding to each of the one or more additional interior chambers and arranged within the housing so that the multiple pixels of each of the additional multi-pixel optical sensors correspond to unique segments of the floor surface within the corresponding additional interior chambers;
   wherein the processing circuit is further configured to receive additional optical data from each of the additional multi-pixel optical sensors and to analyze the additional optical data to detect intrusions of an insect or other object into any of the additional interior chambers.

17. The automated insect monitoring system of claim 16, wherein each of one or more of the additional interior chambers and its corresponding floor surface forms part of a corresponding additional removable chamber, configured so that the additional removable chamber can be separated from a main body of the housing for visual inspection of the floor surface, without damage to the additional removable chamber or the main body of the housing, while leaving the corresponding multi-pixel optical sensor in the main body of the housing.

18. The automated insect monitoring system of claim 1, further comprising an actuator configured to be controlled by the processing circuit and a chemical dispenser, the chemical dispenser comprising a chemical container and a valve operatively coupled to the actuator and configured to allow egress of chemical vapors from the chemical dispenser when the valve is moved to an open or semi-open position by the actuator.

19. The automated insect monitoring system of claim 1, further comprising an actuator configured to be controlled by the processing circuit and a crevice door operatively coupled to the actuator and configured to be moved by the actuator from an open position, in which the crevice is not blocked, to a closed position, in which the crevice is blocked by the crevice door.

* * * * *